(12) United States Patent
Wu

(10) Patent No.: US 11,872,329 B2
(45) Date of Patent: Jan. 16, 2024

(54) CONTAINING APPARATUS FOR VOLATILE LIQUID

(71) Applicant: Aromate Industries Co., Ltd., New Taipei (TW)

(72) Inventor: Han-Yuan Wu, New Taipei (TW)

(73) Assignee: Aromate Industries Co., Ltd., New Taipei (TW)

(*) Notice: Subject to any disclaimer, the term of this patent is extended or adjusted under 35 U.S.C. 154(b) by 826 days.

(21) Appl. No.: 16/796,951

(22) Filed: Feb. 21, 2020

(65) Prior Publication Data

US 2020/0360557 A1    Nov. 19, 2020

(30) Foreign Application Priority Data

May 17, 2019  (TW) .................................. 108117158
Aug. 7, 2019  (TW) .................................. 108128108

(51) Int. Cl.
*A61L 9/12* (2006.01)
*B65D 17/42* (2006.01)
*B65D 17/50* (2006.01)

(52) U.S. Cl.
CPC ................. *A61L 9/12* (2013.01); *B65D 17/42* (2018.01); *B65D 17/501* (2013.01); *A61L 2209/131* (2013.01); *A61L 2209/15* (2013.01)

(58) Field of Classification Search
CPC ......... B65D 17/42; B65D 17/501; A61L 9/12; A61L 2209/131; A61L 2209/133
See application file for complete search history.

(56) References Cited

U.S. PATENT DOCUMENTS

| 9,468,697 B2* | 10/2016 | Gruenbacher ............ A61L 9/04 |
| 2010/0314461 A1* | 12/2010 | Gruenbacher ....... B60H 3/0028 239/6 |
| 2019/0134245 A1* | 5/2019 | Vyas ...................... A01N 43/08 |

FOREIGN PATENT DOCUMENTS

| DE | 102015203808 A1 * | 9/2016 | ............... A61L 9/14 |
| JP | 2012523304 A | 10/2012 | |
| JP | 2018196581 A | 12/2018 | |
| TW | M495854 U | 2/2015 | |
| TW | M577739 U | 5/2019 | |

* cited by examiner

*Primary Examiner* — Jason J Boeckmann
(74) *Attorney, Agent, or Firm* — Li & Cai Intellectual Property Office

(57) ABSTRACT

A containing apparatus for volatile liquid includes a container for receiving a volatile liquid, a breathable membrane, a rupturable substrate, an upper casing, and a pressing member. An accommodating portion of the container has a receiving opening. The rupturable substrate covers the receiving opening for retaining the volatile liquid therein without leakage in a non-use state. The breathable membrane is disposed above the rupturable substrate. The upper casing is disposed above the breathable membrane and has a through-hole. The pressing member is movably connected to the upper casing and can be pressed toward the breathable membrane and the rupturable substrate. The breathable membrane is arranged between the pressing member and the rupturable substrate. A part of the pressing member can pass through the through-hole and break the rupturable substrate to form a breaking hole, yet the breathable membrane is not broken.

14 Claims, 23 Drawing Sheets

CONTAINING APPARATUS FOR VOLATILE LIQUID

CROSS-REFERENCE TO RELATED PATENT APPLICATION

This application claims the benefit of priority to Taiwan Patent Application No. 108117158, filed on May 17, 2019 and Taiwan Patent Application No. 108128108, filed on Aug. 7, 2019. The entire content of the above-identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a containing apparatus for a volatile liquid, and more particularly to a containing apparatus for delivering a volatile liquid such as a car fragrance, car deodorant, indoor fragrance, indoor deodorant, or insecticide.

BACKGROUND OF THE DISCLOSURE

Conventional scented products, such as a car fragrance, car deodorant, indoor fragrance, indoor deodorant, or insecticide, usually use a container to receive a volatile liquid therein. The container has an opening and a sealing film that is attached to the opening to seal the opening, so that the volatile liquid in the container is prevented from vaporizing and the container can be stored and transported easily. When a user wants to use the volatile liquid, the user removes the sealing film from the container, and then the volatile liquid in the container can vaporize into the atmosphere.

However, a manual step is required when removing the sealing film from the container, and this may result in inconvenience for the user. In addition, the opening is completely opened after removing the sealing film, such that a vaporizing speed of the volatile liquid cannot be controlled. Further, the volatile liquid is prone to spill from the container which may result in environmental pollution.

To improve on conventional containing apparatuses for volatile liquids, the applicant of the present disclosure has filed a Taiwan Patent No. TW M495854 "Easy-breaking type containing apparatus for volatile liquid". A breaking device is provided in the containing apparatus for volatile liquid, and is disposed between a sealing film and a breathable film. The sealing film covers an accommodating portion of the containing apparatus for volatile liquid. The breaking device is disposed above the sealing film, and the breathable film is disposed at an upmost position and covers the accommodating portion entirely. When a user wishes to use the containing apparatus, the user only needs to press the breaking device and use the breaking device to break the sealing film, and the volatile liquid can then vaporize into the atmosphere through a breaking hole of the sealing film.

However, the breaking device of the containing apparatus for volatile liquid is disposed between the sealing film and the breathable film, and a height of the containing apparatus is therefore increased. Regardless of whether the containing apparatus is being used or not, the breaking device is always disposed between the sealing film and the breathable film, and cannot be taken out or separated from it.

Because of the reasons described above, there is still room for improvement for the conventional containing apparatuses for volatile liquids.

SUMMARY OF THE DISCLOSURE

In response to the above-referenced technical inadequacies, the present disclosure provides a containing apparatus for volatile liquid, which can be kept in a sealed condition in a transporting or storing process, so as to prevent the volatile liquid from spilling out and vaporizing When a user wants to use the containing apparatus for volatile liquid, a breaking device equipped with the containing apparatus for volatile liquid can be used to break a sealing piece of the containing apparatus, so that the volatile liquid stored in the containing apparatus can vaporize into the atmosphere.

The present disclosure further provides a breaking device, which can be separated from the containing apparatus for volatile liquid regardless of whether the containing apparatus for volatile liquid is used or not. It not only can prevent the sealing film from losing a sealing function, but also lower a height of the containing apparatus for volatile liquid so as to facilitate the transporting or storing process.

In one aspect, the present disclosure provides a containing apparatus for volatile liquid, which includes a container, a rupturable substrate, a breathable membrane, a rear shell, and a pressing member. The container includes an accommodating portion for receiving a volatile liquid. The accommodating portion has a receiving opening. The rupturable substrate covers the receiving opening of the accommodating portion. The breathable membrane is disposed above the rupturable substrate. The rear shell is disposed above the breathable membrane and has a through-hole. The pressing member is movably connected to the rear shell. The breathable membrane is disposed between the pressing member and the rupturable substrate. A part of the pressing member passes through the through-hole of the rear shell and is configured to break the rupturable substrate to form a breaking hole. The breathable membrane is stretchable and not broken by the pressing member, so that the volatile liquid passes through the breaking hole of the rupturable substrate and is absorbed by the breathable membrane for vaporizing into the atmosphere.

Therefore, the present disclosure provides the pressing member, which is movably connected to the rear shell and the breathable membrane, which is arranged between the pressing member and the rupturable substrate. A part of the pressing member is configured to pass through the through-hole of the rear shell for breaking the rupturable substrate so as to form a breaking hole. Meanwhile, the breathable membrane has resilience and is not broken by the pressing member, so that the volatile liquid can flow out through the breaking hole of the rupturable substrate and is absorbed by the breathable membrane for vaporizing into the atmosphere. Therefore, the containing apparatus for volatile liquid of the present disclosure can retain the volatile liquid under the rupturable substrate during the transporting or storage process. When the user wants to use the containing apparatus for volatile liquid, he/she only needs to press the pressing member to break the rupturable substrate, so that the containing apparatus for volatile liquid is not retained in a sealed condition. Therefore, the containing apparatus for volatile liquid of the present disclosure can be stored more easily.

The present disclosure has other beneficial effects such as, regardless of whether the containing apparatus for volatile liquid is being used or not, the pressing member can be separated from a housing of the containing apparatus for volatile liquid, or can be stored in a storage position. Such configuration not only can prevent the rupturable substrate from losing the sealing function by accident, it can also lower the height of the containing apparatus for volatile liquid. Therefore, the containing apparatus for volatile liquid of the present disclosure can be stored and transported easily These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
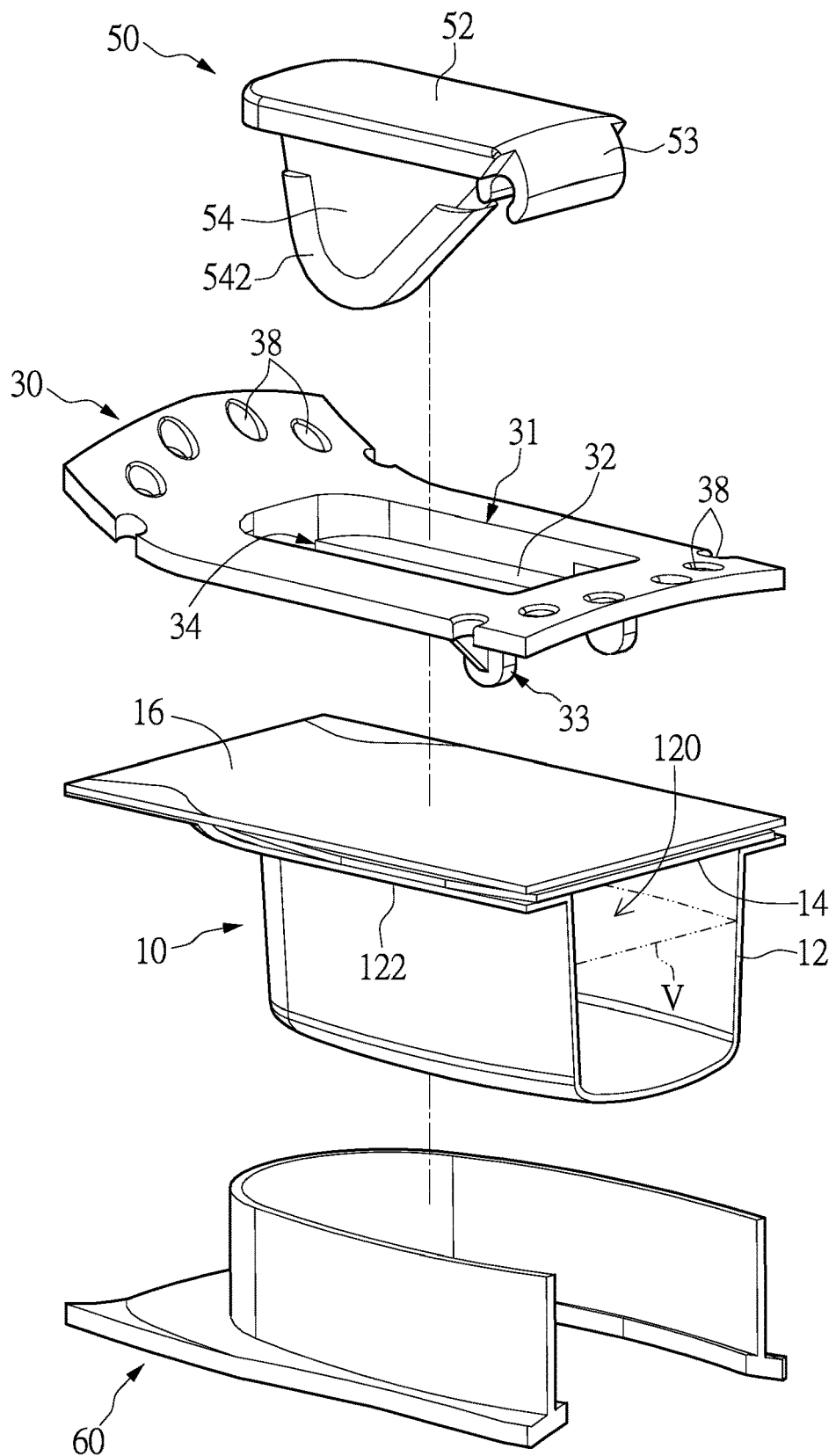
FIG. 1 is a partial exploded perspective view of a containing apparatus for volatile liquid of a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Figure 2:
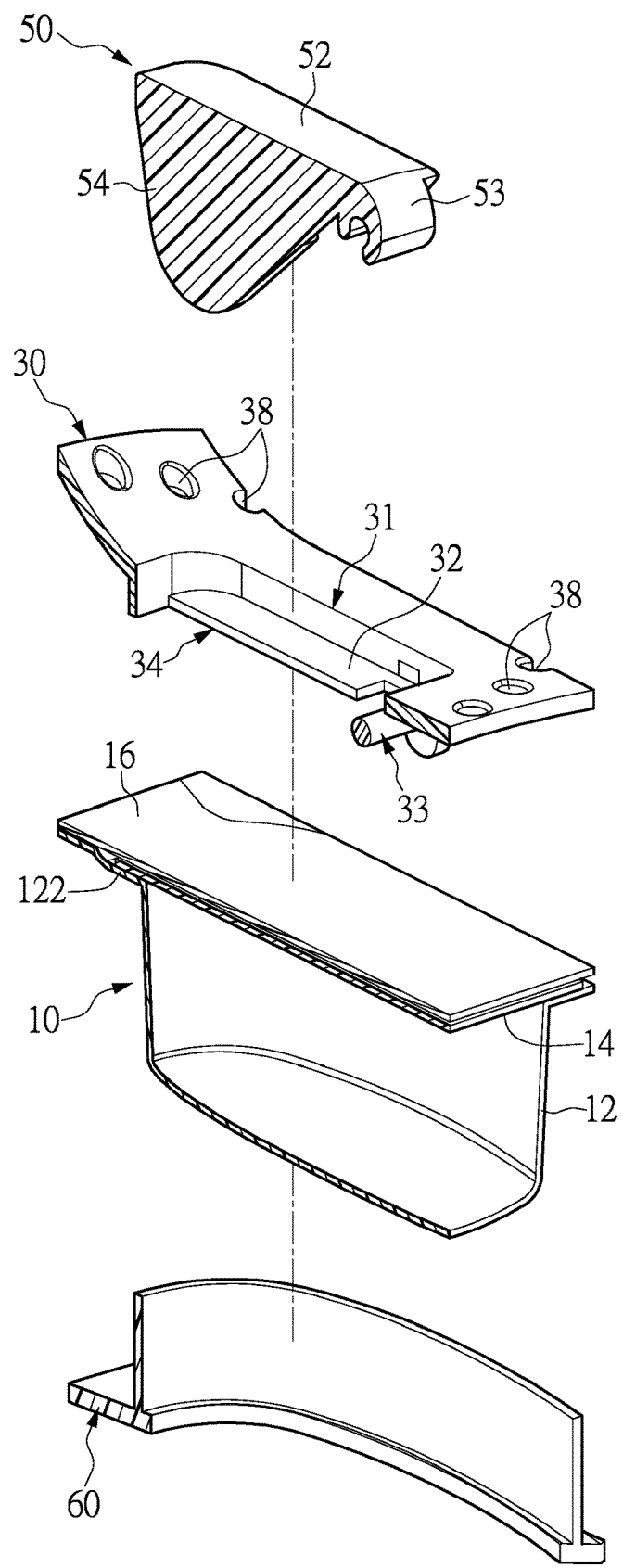
FIG. 2 is an exploded cross-sectional view of the containing apparatus for volatile liquid of the first embodiment of the present disclosure.
Figure 3:
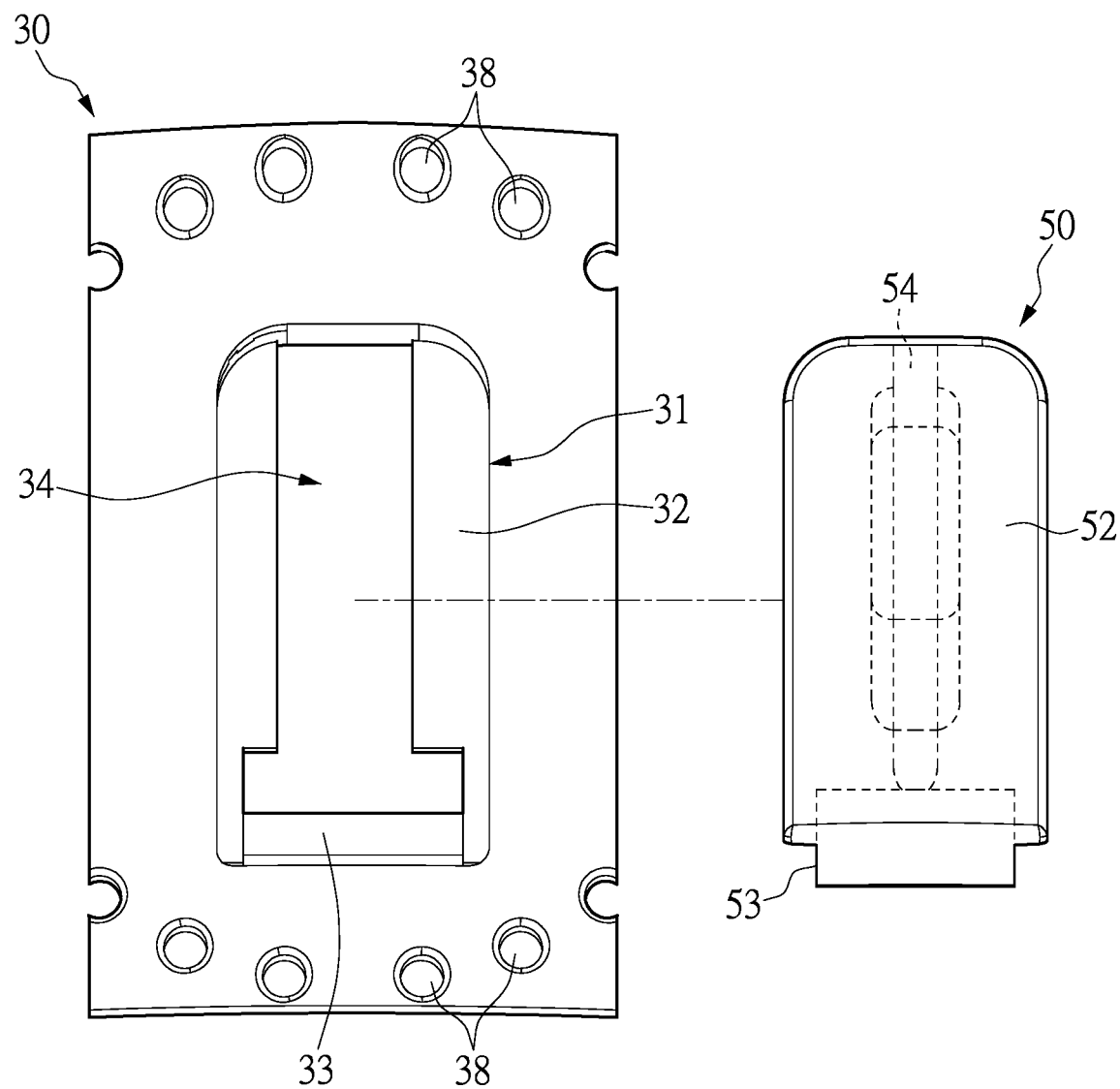
FIG. 3 is a top view of a rear shell and a pressing member of the first embodiment of the present disclosure.
Figure 4:
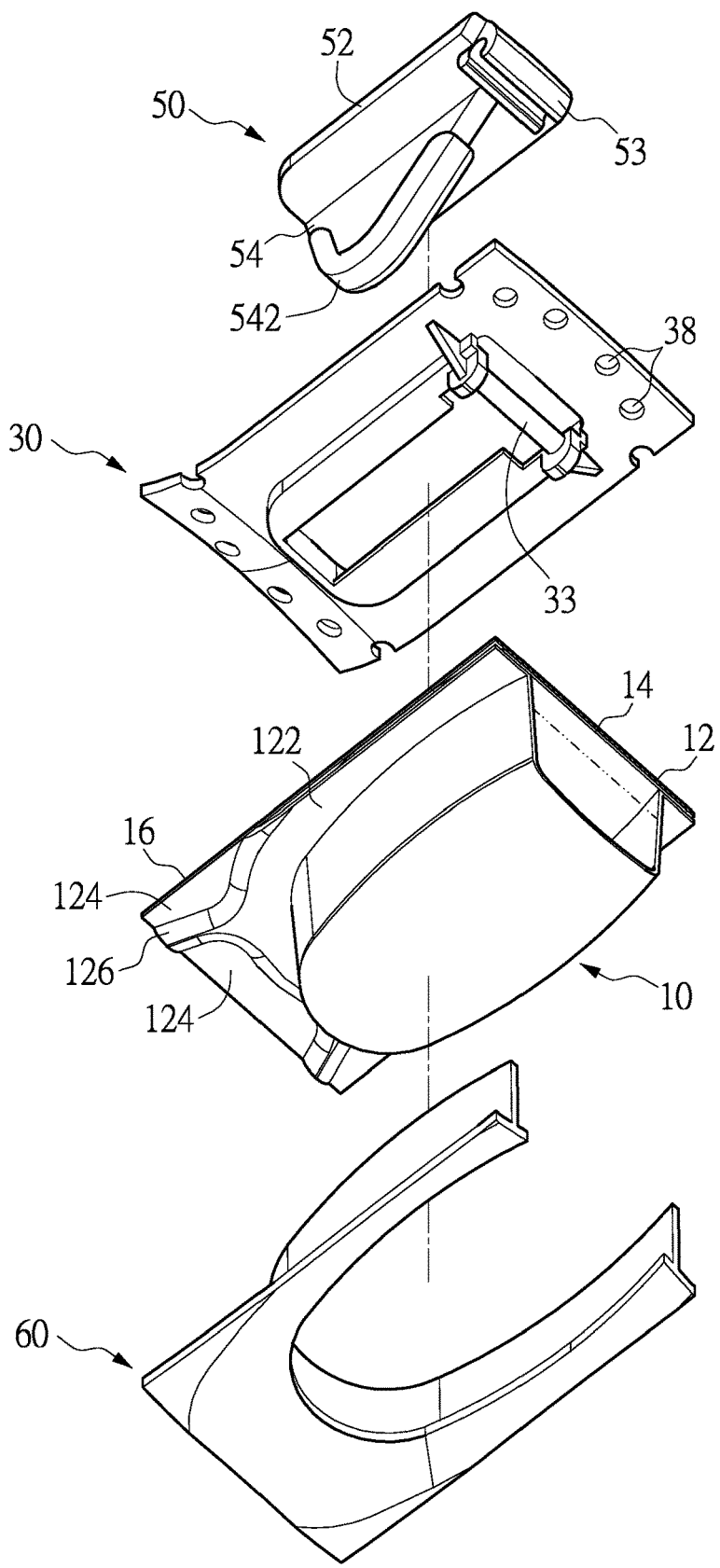
FIG. 4 is another partial exploded perspective view of the containing apparatus for volatile liquid of the present disclosure.

Reference is made to FIG. 1 to FIG. 4. FIG. 1 and FIG. 4 are partial exploded perspective views of a containing apparatus for volatile liquid of the present disclosure. FIG. 2 is an exploded cross-sectional view of the containing apparatus for volatile liquid of the present disclosure. FIG.

3 is a top view of a rear shell and a pressing member of the present disclosure. Figures in this embodiment are partial figures, and a portion of each of four sides of the containing apparatus for volatile liquid are cut away. This embodiment provides a containing apparatus for volatile liquid, which includes a container 10, a rupturable substrate 14, a breathable membrane 16, a rear shell 30, a pressing member 50, and an external casing 60.

The container 10 is used to receive a volatile liquid V, and includes an accommodating portion 12. A receiving opening 120 is formed on a top end of the accommodating portion 12. The accommodating portion 12 can be made of plastic material. In this embodiment, the accommodating portion 12 has an inner rim 122 extending outward from a top edge thereof. The rupturable substrate 14 is adhered to the inner rim 122. The accommodating portion 12 of this embodiment further has an outer rim 124 extending outwardly from the inner rim 122. A height deviation is formed between the inner rim 122 and the outer rim 124. From a top view, the outer rim 124 is located on a periphery of the inner rim 122. The rupturable substrate 14 is adhered to the top surface of the inner rim 122. For example, a hot-press manner can be applied to attach the rupturable substrate 14 to the inner rim 122. In this embodiment, since the portions of the inner rim 122 are cut away, only one side of the inner rim 122 is shown at a time. In truth, the inner rim 122 is annular-shaped.

The rear shell 30 and the external casing 60 can be combined to form one casing for receiving the container 10. The outer rim 124 of the container 10 abuts against a top edge of the external casing 60. The volatile liquid V means a liquid with volatility, such as aromatic, deodorant, or insecticide. However, the present disclosure is not limited thereto, and the container 10 can be used to receive solid material, such as camphor or exsiccator.

In this embodiment, the rupturable substrate 14 covers the receiving opening 120 of the container 10. The breathable membrane 16 is disposed above the rupturable substrate 14. The breathable membrane 16 of this embodiment is adhered to the outer rim 124 of the accommodating portion 12. For example, a hot-pressing manner can be applied to attach the breathable membrane 16 to the outer rim 124. A height deviation between the inner rim 122 and the outer rim 124 is larger than or equal to a height of the rupturable substrate 14. The height deviation benefits the breathable membrane 16 to be welded well to the outer rim 124 during hot-pressing process, and not be affected by the rupturable substrate 14. The rupturable substrate 14 provides a sealing function, so that the volatile liquid V can be stored in the container 10 without vaporizing and can be stored for a long time. The breathable membrane 16 can be made of porous material (e.g., a nonwoven fabric) or a film that is slim and formed with a plurality of interstices (e.g., a polyolefin elastomer (POE) film) The breathable membrane 16 not only has the characteristics of being breathable, but also has a capillary function which can help to diffuse the volatile liquid.

In this embodiment, the rupturable substrate 14 can be a tin foil, an aluminum foil, or a kraft paper, but it is not limited to the above examples. Any material with airtightness and able to resist erosion from the volatile liquid can be considered as a material for the rupturable substrate 14. In this embodiment, preferably, an extensibility of the breathable membrane 16 is larger than that of the rupturable substrate 14. The bursting strength of the rupturable substrate 14 is preferably smaller than that of the breathable membrane 16. The breathable membrane 16 of this embodiment has a higher tensile strength and tearing strength, so that it can endure a predetermined deformation when the pressing member 50 is pressed downward. The polyolefin elastomer has a larger tensile strength and a larger tearing strength with better tenacity and flexibility. The polyolefin elastomer POE also has excellent thermal-welding property.

Figure 8:
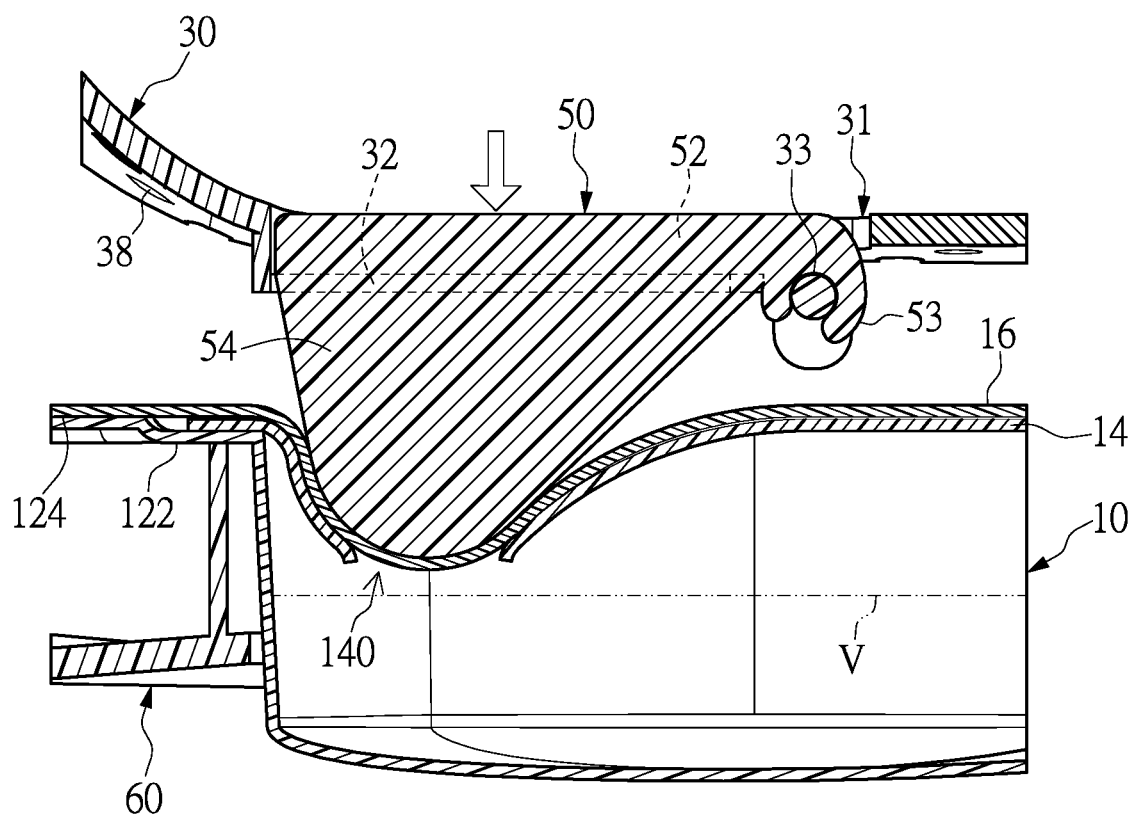
FIG. 8 is a cross-sectional view of the containing apparatus for volatile liquid in the use state of the present disclosure.

The rear shell 30 is disposed above the breathable membrane 16, and has a through-hole 34. The pressing member 50 is movably connected to the rear shell 30. The breathable membrane 16 is disposed between the pressing member 50 and the rupturable substrate 14. A part of the pressing member 50 passes through the through-hole 34 of the rear shell 30 to break the rupturable substrate 14 to form a breaking hole 140, yet the breathable membrane 16 has flexibility and is not broken by the pressing member 50. The volatile liquid V therefore passes through the breaking hole 140 of the rupturable substrate 14 and the breathable membrane 16 and vaporizes (as shown in FIG. 8).

Moreover, referring to FIG. 4, the accommodating portion 12 further has a passage 126 formed between the inner rim 122 and the outer rim 124. The passage 126 is configured to allow for volatile liquid circulation. When a user presses the pressing member 50, the volatile liquid coming out from the break hole 140 between the breathable membrane 16 and the rupturable substrate 14 can be circulated through the passage 126.

Figure 6:
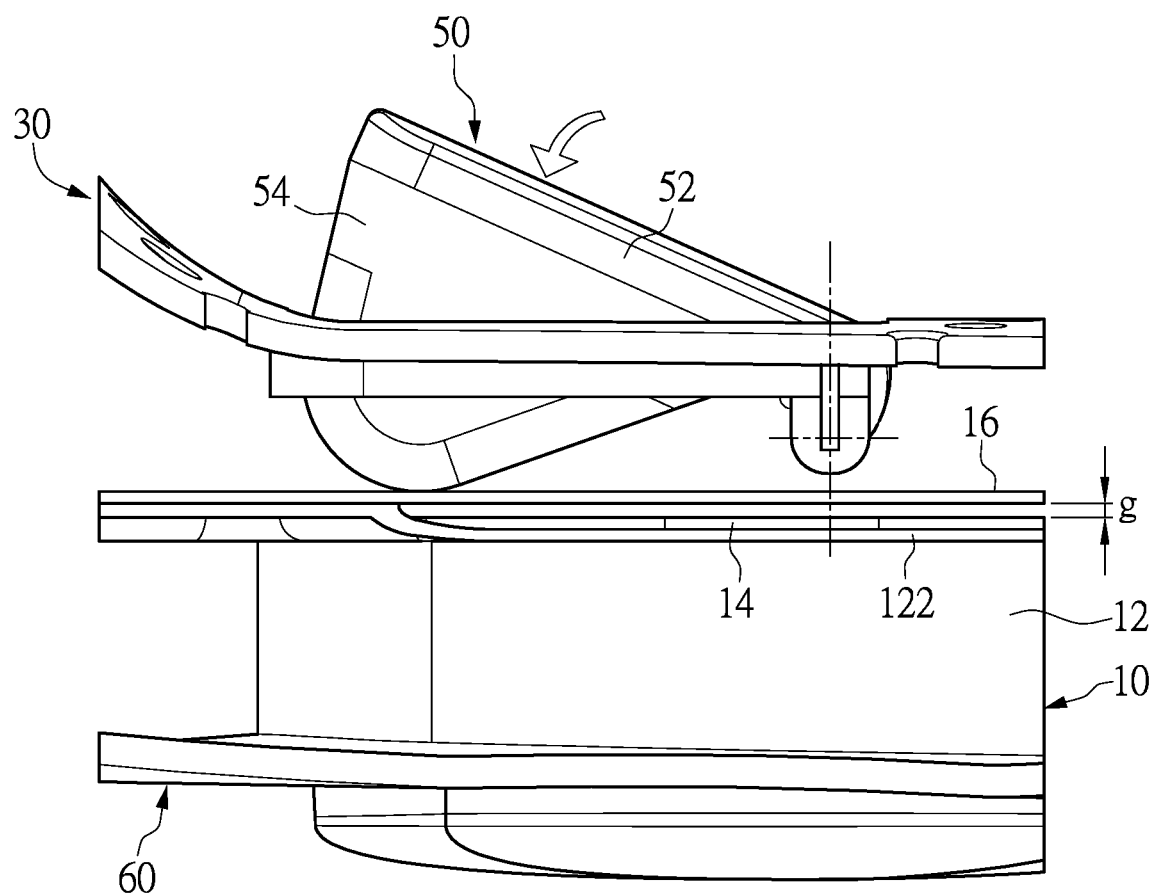
FIG. 6 is a cross-sectional view of the containing apparatus for volatile liquid (non-used) of the present disclosure.

According to a practical embodiment of the present disclosure, the rupturable substrate 14 and the breathable membrane 16 are close to each other. A distance g between the rupturable substrate 14 and the breathable membrane 16 is approximately from 0.2 mm to 7 mm (as shown in FIG. 6). The distance g is formed due to a height deviation between the inner rim 122 and the outer rim 124, and the distance g is preferably as small as possible. In addition, the distance g of this embodiment can be adjusted by an extending height of the inner rim 122. When the rupturable substrate 14 is broken to form the breaking hole 140, the volatile liquid V contacts the breathable membrane 16. Because the breathable membrane 16 has tiny pores with capillarity, the volatile liquid can easily diffuse and vaporize through the breaking hole 140 of the rupturable substrate 14.

The pressing member 50 of this embodiment can be an integrated plastic piece manufactured by injection molding and functioning as a breaking device, but a material of the pressing member 50 is not limited thereto. For example, the pressing member 50 can be made of metal or other materials that is durable enough to exert a pressing force. The pressing member 50 includes a top board 52, and a penetration plate 54 that is connected to a bottom surface of the top board 52. One side of the top board 52 is pivotally connected to the rear shell 30. The penetration plate 54 passes through the through-hole 34 of the rear shell 30 and is configured to downwardly press on the breathable membrane 16 and rupturable substrate 14. The breathable membrane 16 has resilience and is not broken by the pressing member 50. The penetration plate 54 breaks the rupturable substrate 14. However, the pressing member 50 of the present disclosure is not limited to the above structure. For example, the penetration plate of the pressing member can lie flat on a bottom surface of the top board, and be erected on the bottom surface of the top board when required for use.

In this embodiment, the rear shell 30 is located on an outmost side of the containing apparatus for volatile liquid (as shown in the figures). The rear shell 30 can be a decorative piece having a function of receiving the pressing member 50. The rear shell 30 has a basin portion 31. The basin portion 31 is formed concavely on a top surface of the rear shell 30. The through-hole 34 is formed on a bottom board 32 of the basin portion 31 and is configured to be a limiting mechanism to restrict positions of the pressing member 50. When the pressing member 50 is located in a pressed-down position, the top board 52 of the pressing member 50 is received in the basin portion 31, and the penetration plate 54 is exposed from the bottom of the rear shell 30. In addition, the rear shell 30 of this embodiment further has a plurality of vents 38 that allows the vapors of the volatile liquid V to flow out through the vents 38.

Moreover, the rear shell 30 of this embodiment can be separated from the container 10 during transportation or storage. Therefore, a total height can be reduced and storing space required can be reduced. When in use, the rear shell 30 covers on the container 10.

A connecting manner of the pressing member 50 and the rear shell 30 according to this embodiment is introduced with an example as follows. The rear shell 30 has a rotary shaft 33 that is disposed at one end of the through-hole 34. The pressing member 50 has a pivoting portion 53 that is rotatably connected to the rotary shaft 33.

More specifically, the pivoting portion 53 of the pressing member 50 is perpendicular to the penetration plate 54, and the through-hole 34 of the rear shell 30 is T-shaped and corresponds to a shape of the pressing member 50. The rotary shaft 33 is located in the through-hole 34. By the above arrangement, this embodiment provides a limiting mechanism for restricting the positions of the pressing member 50, so as to prevent the pressing member 50 from being pressed excessively. In addition, two sides of the penetration plate 54 of the pressing member 50 each have a bulge portion 542. The bulge portion 542 makes a bottom of the pressing member 50 smoother and less sharp.

Figure 5:
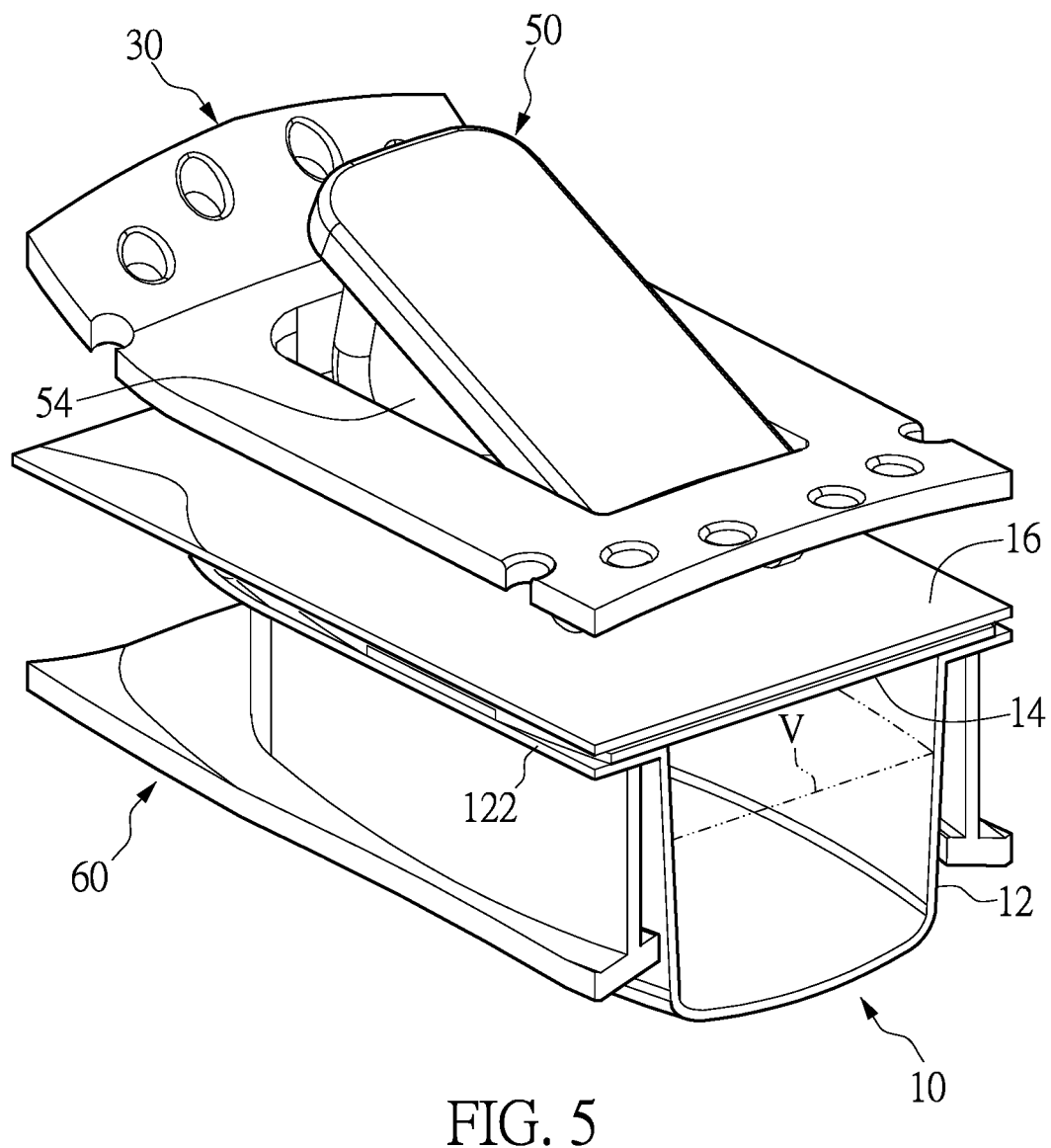
FIG. 5 is an assembled perspective view of the containing apparatus for volatile liquid (non-used) of the present disclosure.

Reference is made to FIG. 5, which is an assembled perspective view of the containing apparatus for volatile liquid of the present disclosure. The pressing member 50 is located in a non-pressing position. In this embodiment, an acute angle is included between a top surface of the pressing member 50 and a top surface of the rear shell 30. The included angle can be from 20 degrees to 35 degrees.

Reference is made to FIG. 6, which is a cross-sectional assembled view of the containing apparatus for volatile liquid (in a non-use state) of the present disclosure. When the user wants to use the containing apparatus for volatile liquid, a force is exerted to the top board 52 of the pressing member 50. The farther away (the user) is from the rotary shaft 33, the more labor can be saved.

Figure 7:
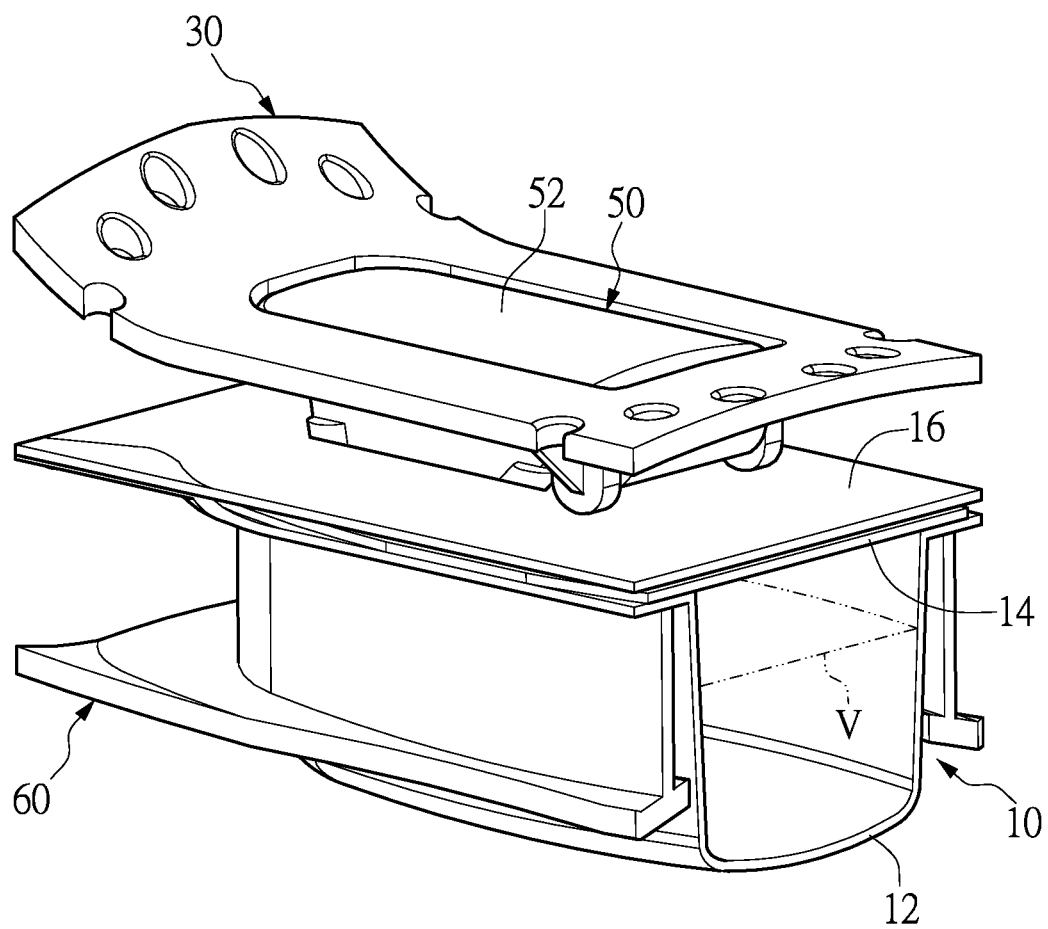
FIG. 7 is a perspective view of the containing apparatus for volatile liquid in a use state of the present disclosure.

Reference is made to FIG. 7 and FIG. 8, which are a perspective and a cross-sectional assembled view of the containing apparatus for volatile liquid (in a use state) of the present disclosure. The pressing member 50 is located at a pressed-down position, the top board 52 of the pressing member 50 is received in the basin portion 31, and the penetration plate 54 is exposed from the bottom of the rear shell 30.

Figure 9:
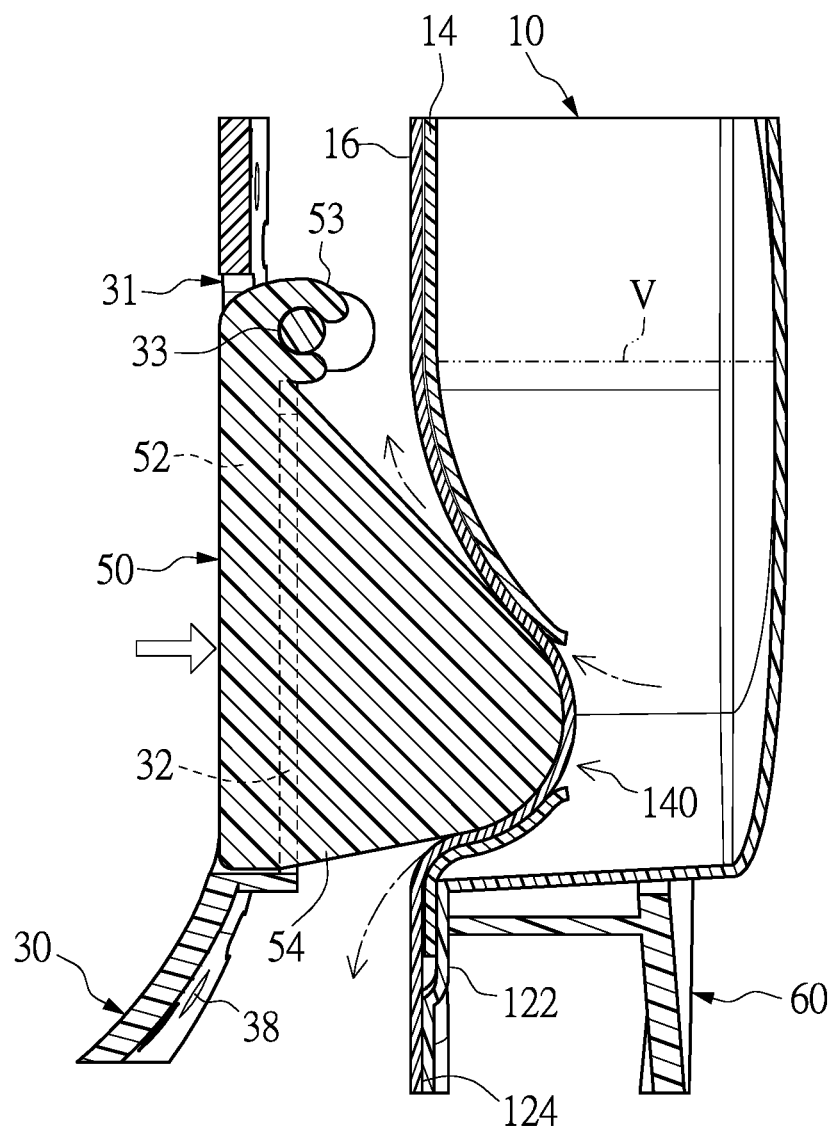
FIG. 9 is a cross-sectional schematic view of the containing apparatus for volatile liquid in the use state of the present disclosure.

Reference is made to FIG. 9, which is a cross-sectional schematic view of the containing apparatus for volatile liquid in the use state of the present disclosure. According to the present disclosure, after the rupturable substrate 14 of the containing apparatus for volatile liquid is broken, a preferable usage is to put the containing apparatus for volatile liquid in an erected state, so as to control the release of the volatile liquid. For example, it can be disposed on a table, or in a hanging condition. Therefore, by gravity, the volatile liquid can flow through the breaking hole 140 of the rupturable substrate 14 to the breathable membrane 16. The volatile liquid is absorbed by the breathable membrane 16 and is slowly released to vaporize into the atmosphere. It should be noted that, the position of the pressing member 50 is preferably close to the bottom of the container 10, so that the volatile liquid flow out more completely and vaporize.

Second Embodiment

Reference is made to FIGS. 10 to 14, which illustrate the containing apparatus for volatile liquid of another embodiment of the present disclosure. The second embodiment of this present disclosure provides the containing apparatus for volatile liquid, which includes a container 10a, a rear shell 30a, an adjusting element 40a, a pressing member 50a, and an external casing 60a. As shown in FIG. 15, the container 10a is similar to the first embodiment, which includes a rupturable substrate 14 and a breathable membrane 16a. The main feature of this embodiment is that, the pressing member 50a not only can break the rupturable substrate 14, but also can function as a clip. For example, the containing apparatus for volatile liquid can be clipped onto an air vent blade of a mobile device. In addition, the adjusting element 40a can provide a function of adjusting a vaporizing amount by cooperating with the rear shell 30a.

The pressing member 50a of this embodiment includes a clipping portion 56, and a penetration plate 54. The penetration plate 54 is connected to one end of the clipping portion 56. The clipping portion 56 is connected pivotally to the rear shell 30a. More specifically, in this embodiment, the connecting manner of the pressing member 50a and the rear shell 30a is that, the clipping portion 56 has a rotary shaft 561, the rear shell 30a has a pivoting portion 35, and the rotary shaft 561 is rotatably connected to the pivoting portion 35. However, the present disclosure is not limited thereto. For example, positions of the rotary shaft and the pivoting portion are changeable. By rotating the pressing member 50a, the penetration plate 54 can pass through the through-hole 34 of the rear shell 30a and inwardly press the breathable membrane 16 and the rupturable substrate 14. However, the breathable membrane 16 is with flexibility and is not broken by the pressing member 50a, and the penetration plate 54 breaks the rupturable substrate 14.

In this embodiment, the rear shell 30a is located at an outmost side of the containing apparatus for volatile liquid. Another function of the rear shell 30a is to be combined with the adjusting element 40a for adjusting a vaporizing speed. The rear shell 30a of this embodiment further has a plurality of vent holes 38, through which the volatile liquid V can vaporize. A plurality of adjusting openings 422 are formed on the adjusting element 40a, which correspond to the vent holes 38 of the rear shell 30a. The adjusting element 40a is rotatably mounted to one side of the rear shell 30a, so that the adjusting openings 422 and the vent holes 38 cooperatively form an adjustable ventilation area.

Figure 10:
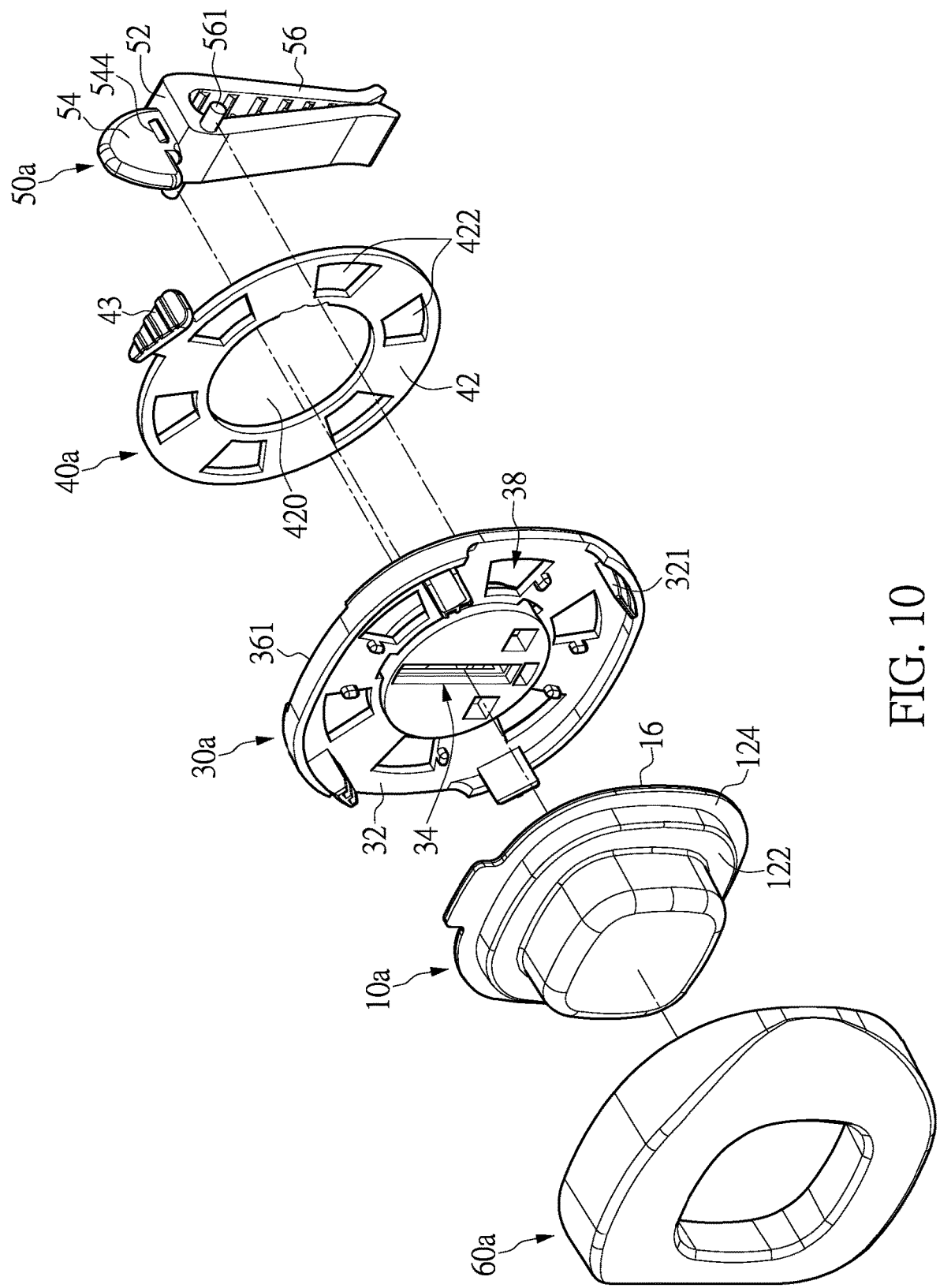
FIG. 10 is an exploded perspective view of the containing apparatus for volatile liquid of a second embodiment of the present disclosure.
Figure 11:
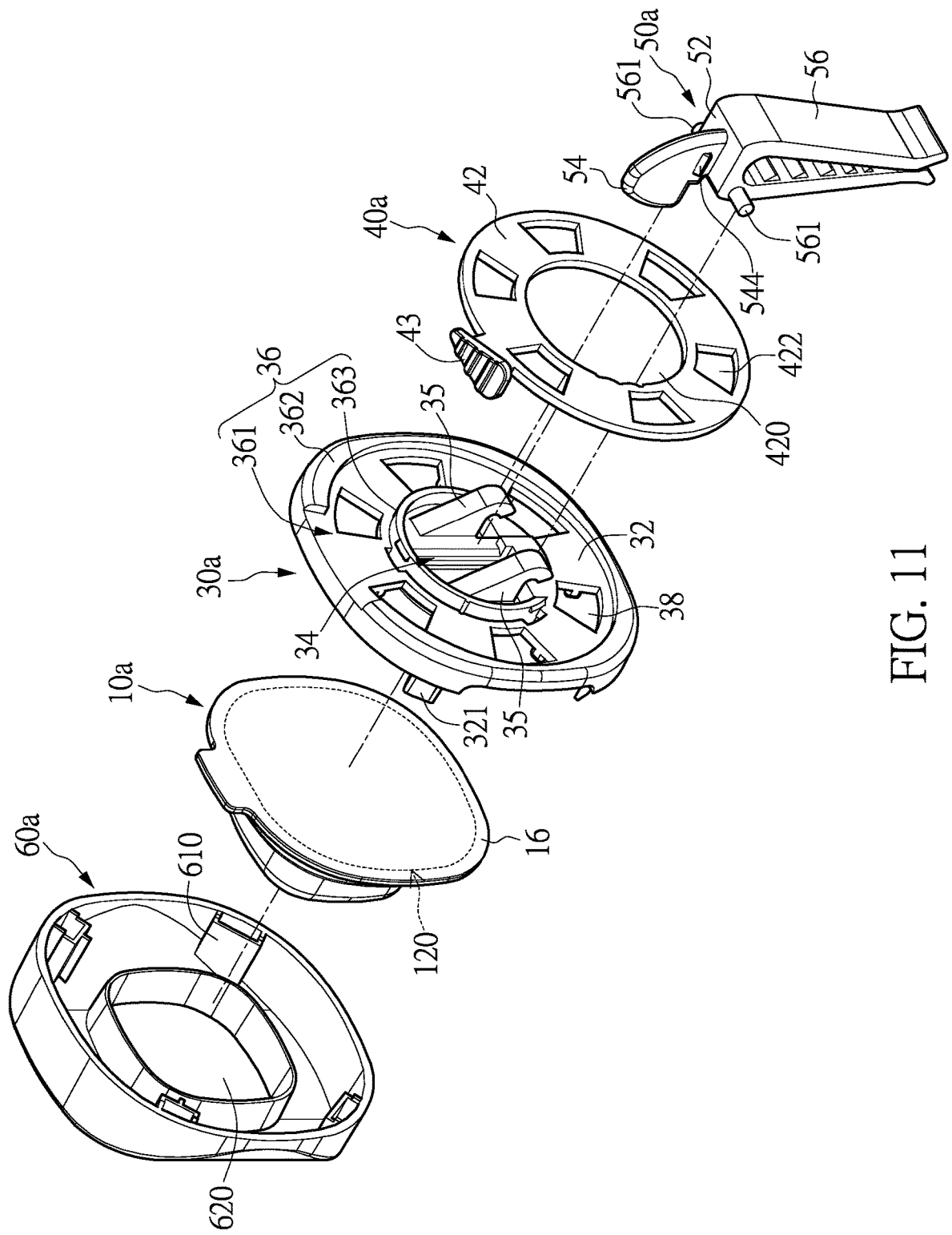
FIG. 11 is another exploded perspective view of the containing apparatus for volatile liquid of the second embodiment of the present disclosure.
Figure 12:
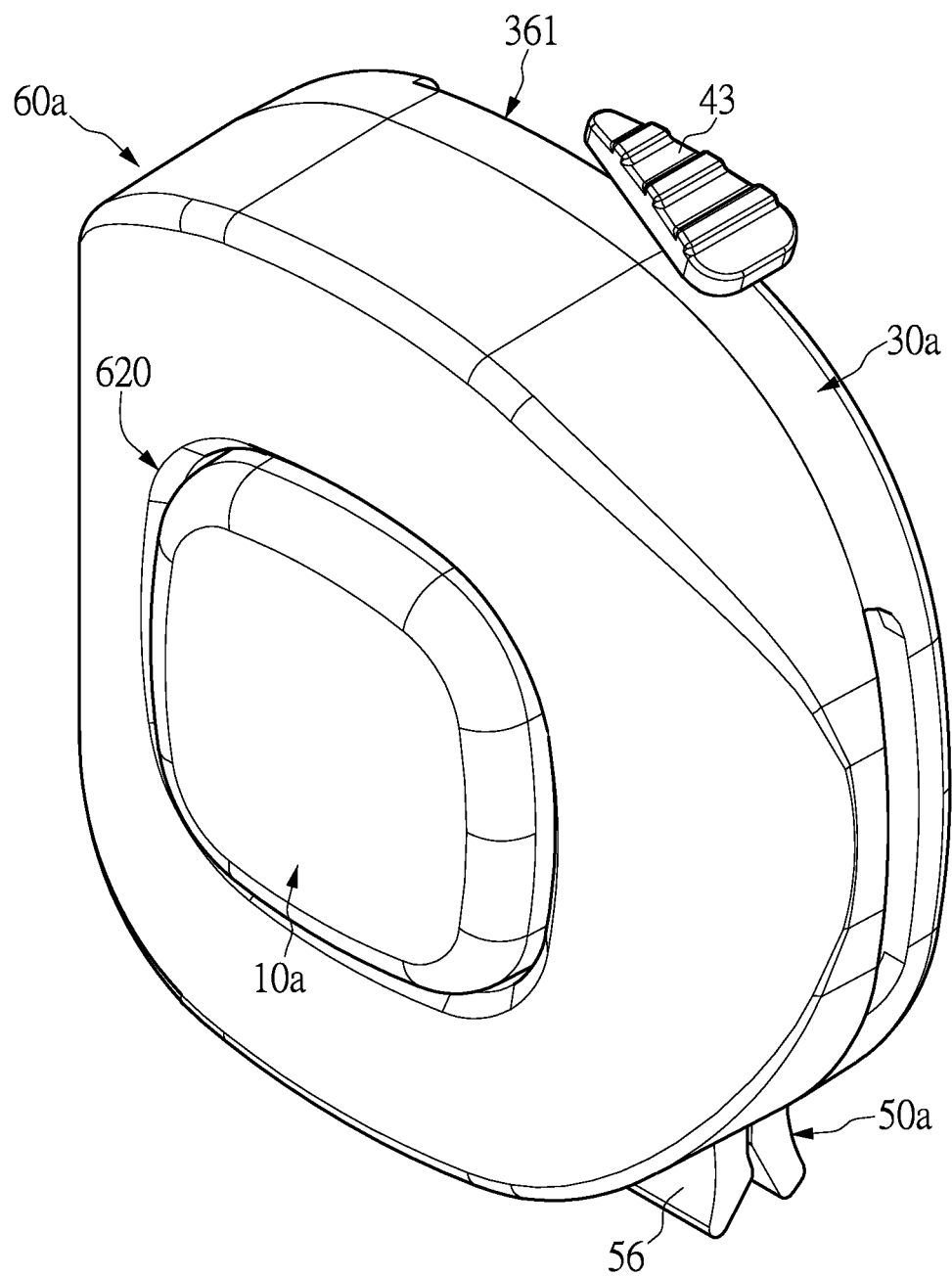
FIG. 12 is an assembled perspective view of the containing apparatus for volatile liquid of the second embodiment of the present disclosure.

As shown in FIG. 10 and FIG. 11, the adjusting element 40a includes an annular-shaped ring portion 42 that includes a mounting opening 420. The adjusting element 40a includes a grip portion 43 that is formed on an edge of the adjusting element 40a. The user can rotate the grip portion 43 to change a position of the adjusting opening 422 of the adjusting element 40a. The rear shell 30a includes a mounting portion 36, and the mounting opening 420 of the adjusting element 40a is rotatably connected to the mounting portion 36.

For example, as shown in FIG. 11, the mounting portion 36 includes an outer annular portion 362 and an inner annular portion 363. The inner annular portion 363 is formed on a periphery of the through-hole 34. The outer annular portion 362 is formed on a periphery of the rear shell 30a.

The inner annular portion 363 is engaged with an inner edge of the mounting opening 420 of the adjusting element 40a. The outer annular portion 362 has a position-limiting cutout 361, and the grip portion 43 is movably disposed in the position-limiting cutout 361, so as to limit a displacement range of the grip portion 43.

In this embodiment, the rear shell 30a and the external casing 60a are combined as a casing to receive the container 10a. A combination manner of the external casing 60a and the rear shell 30a can be engagement or adhesion. According to the embodiment, the external casing 60a includes a plurality of hooking holes 610, and the rear shell 30a has a plurality of hooks 321 formed on a periphery of the rear shell 30a, so that the external casing 60a can be engaged with the rear shell 30a. The external casing 60a further includes an observation window 620, and a part of the container 10a is exposed from the observation window 620 for observing a remained value of the volatile liquid.

Figure 13:
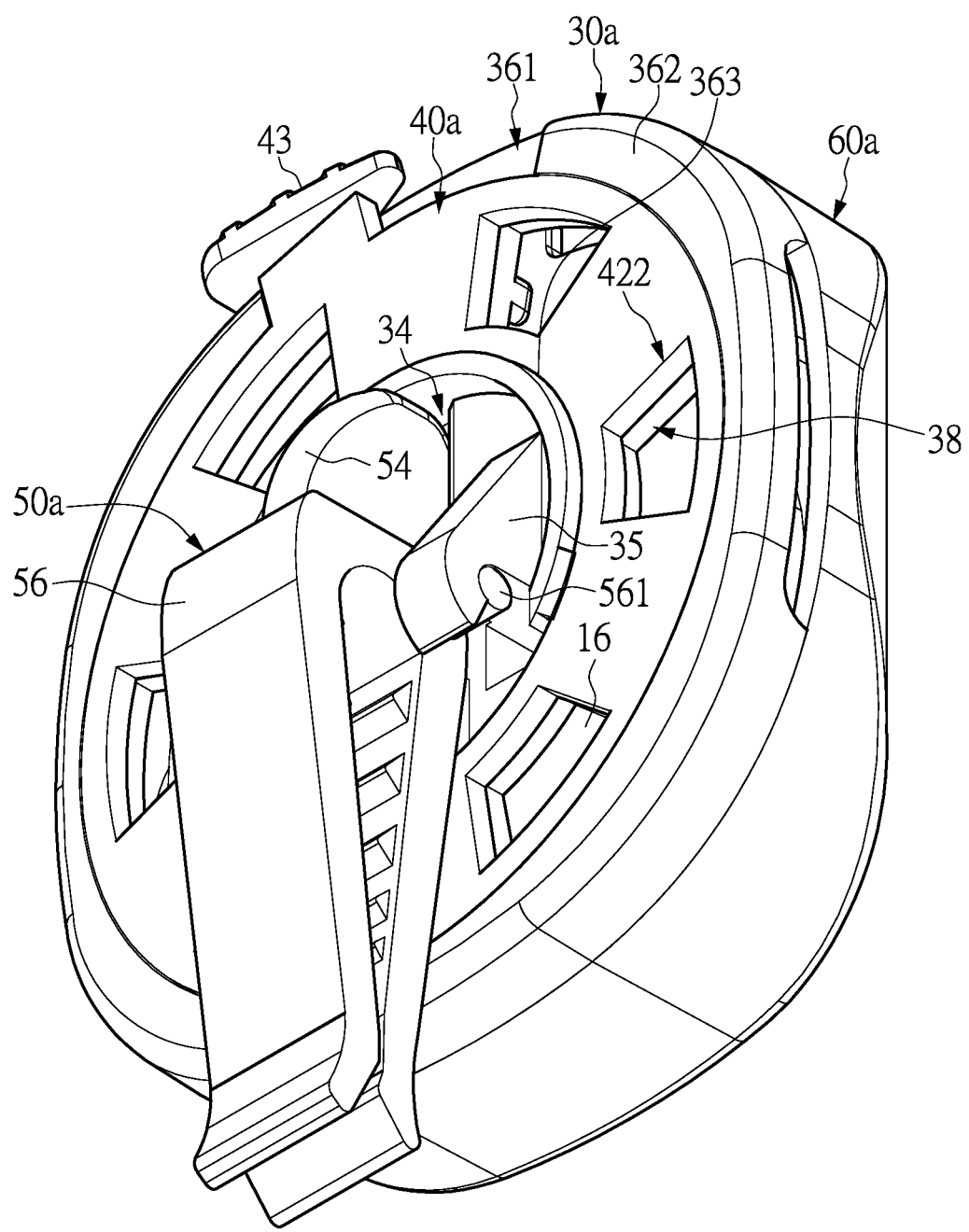
FIG. 13 is another assembled perspective view of the containing apparatus for volatile liquid of the second embodiment of the present disclosure.
Figure 14:
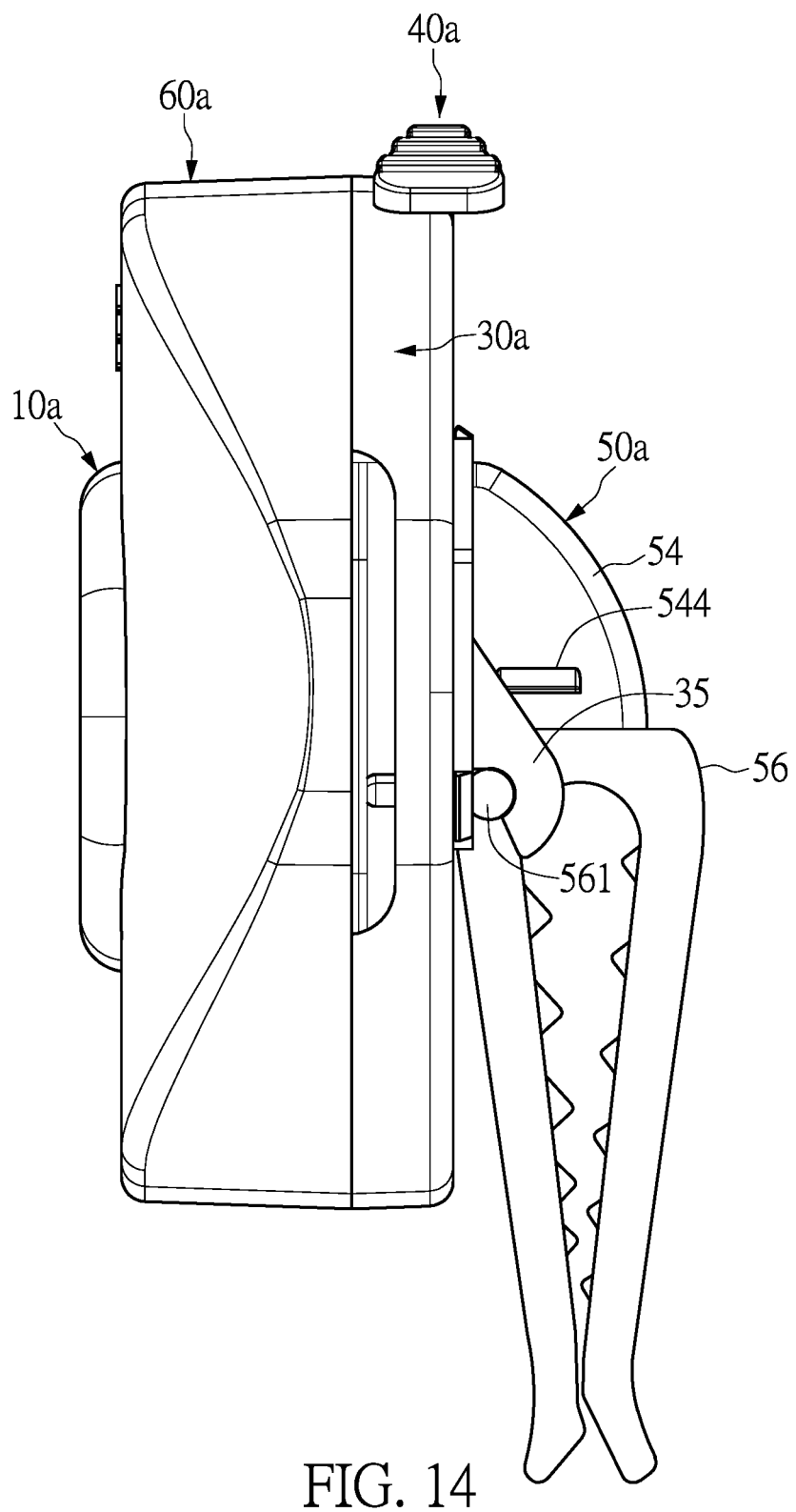
FIG. 14 is a side view of the containing apparatus for volatile liquid of the second embodiment of the present disclosure.
Figure 15:
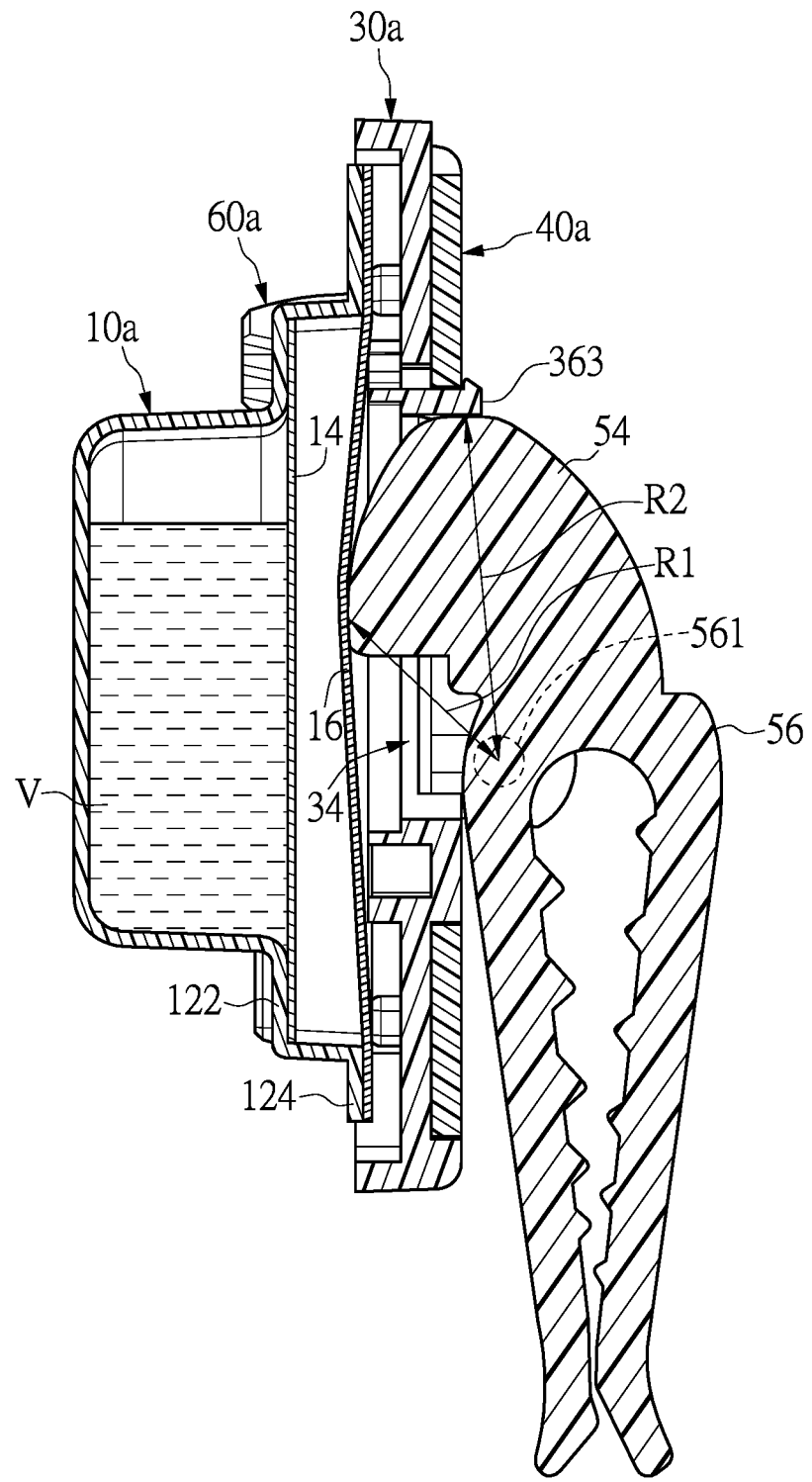
FIG. 15 is a cross-sectional view of the containing apparatus for volatile liquid of the second embodiment in a storage state of the present disclosure.

Reference is made to FIG. 13 to FIG. 15, which illustrate the containing apparatus for volatile liquid with the pressing member being arranged in a storage (or non-use) state according to the present disclosure. The storage state means that the pressing member 50a is in a position where it is at rest not pressing into the rupturable substrate 14 and breathable membrane 16 of container 10a. The rotary shaft 561 of the pressing member 50a is rotatably connected to the pivoting portion 35 of the rear shell 30a, so that the pressing member 50a can rotate around the rotary shaft 561, which functions as an axis. A top end of the pressing member 50a of this embodiment is straight-shaped, and abuts against the inner annular portion 363, so that the pressing member 50a can be properly fixed in the storage state to prevent an accidental rotation.

A shape of the pressing member 50a is introduced in detail as follows. As shown in FIG. 15, the rotary shaft 561 of the pressing member 50a is substantially perpendicular to the penetration plate 54. The through-hole 34 of the rear shell 30a is linear-shaped and corresponds to a shape of the pressing member 50a. A distance between one side of the penetration plate 54 that is closer to the container 10a and the axis is smaller than a distance between a top end of the penetration plate 54 and the axis. More specifically, the side of the penetration plate 54 that is closer to the container 10a is smoother and is slightly arc-shaped (in other words, the left side of the penetration plate 54 as shown in FIG. 15). In other words, the distance R1 between a left side of the penetration plate 54 and the rotary shaft 561 is shorter, and the distance R2 between the top end of the penetration plate 54 and the rotary shaft 561 is longer. The top end of the penetration plate 54 is more curved with a substantially short and straight portion. Another side of the penetration plate 54 distant from the container 10a is smoother (in other words, the right side of the penetration plate 54 as shown in FIG. 15).

Figure 16:
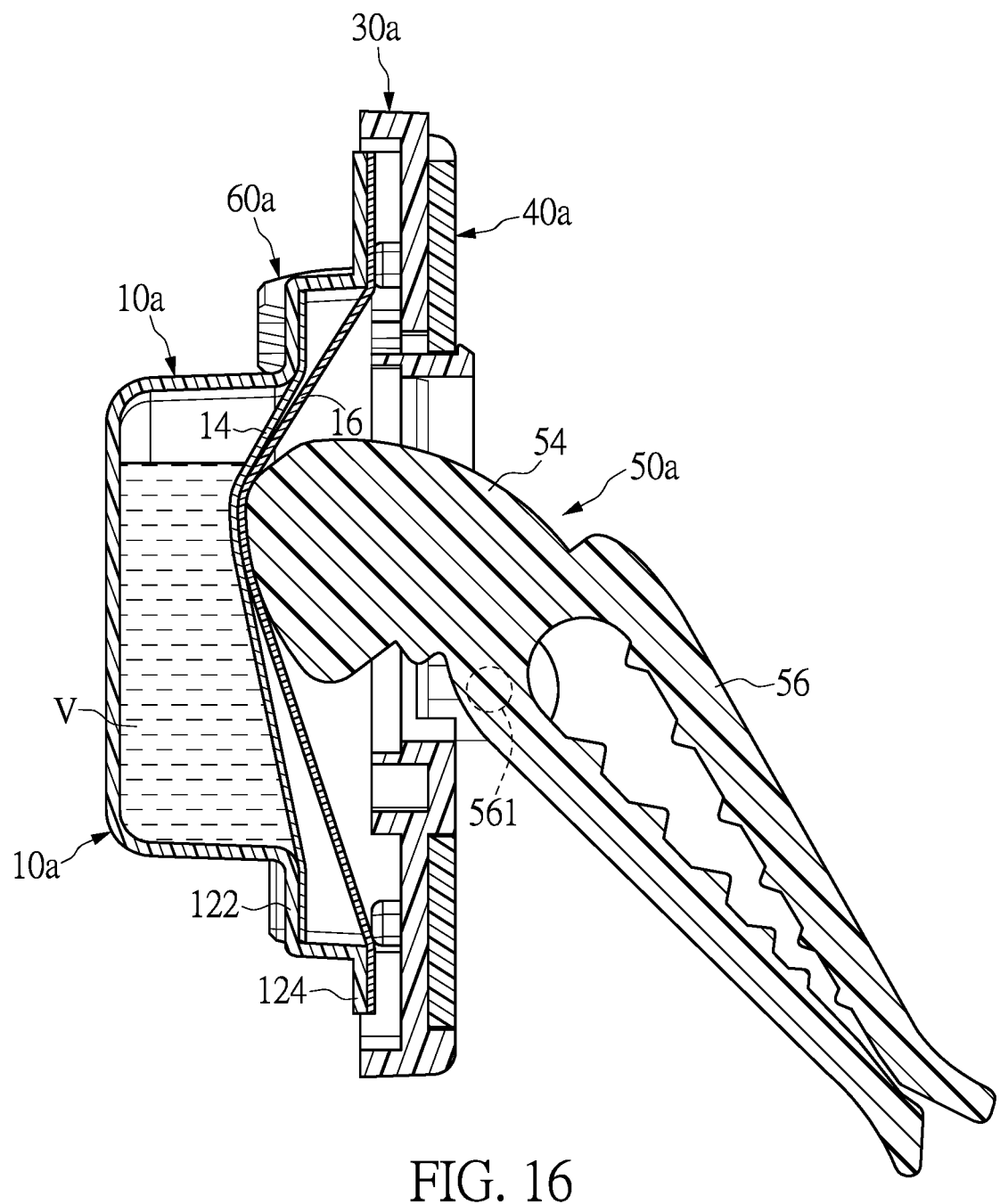
FIG. 16 is a cross-sectional view of the containing apparatus for volatile liquid of the second embodiment in a preparing step of the present disclosure.

Referring to FIG. 16, an expanding process of the containing apparatus for volatile liquid is shown in a cross-sectional view. When the user wants to use the containing apparatus for volatile liquid, the user rotates the pressing member 50a, and the clipping portion 56 is outwardly pulled toward a direction away from the container 10a, that is, in a counterclockwise direction as shown in FIG. 16. By the above-mentioned design of the pressing member 50a, when the pressing member 50a rotates around the rotary shaft 561, the top end of the penetration plate 54 moves closer to an inner part of the container 10a. The penetration plate 54 of the pressing member 50a first inwardly presses against the breathable membrane 16, and then against the rupturable substrate 14.

More specifically, the rupturable substrate 14 can be an aluminum foil, which has a thickness of approximately from 18 μm to 75 μm. In this embodiment, preferably, a flexibility of the breathable membrane 16 is larger than that of the rupturable substrate 14. A bursting strength of the rupturable substrate 14 is smaller than that of breathable membrane 16. The breathable membrane 16 of this embodiment preferably has stronger tensile strength and tearing strength, so that it can endure a predetermined deformation when the pressing member 50a is pressed downward. For example, an elongation rate of the breathable membrane 16 can be from 200% to 990%. In this embodiment, preferably, the elongation rate of the breathable membrane 16 is from 700% to 990%. The polyolefin elastomer has larger tensile strength and a larger tearing strength with better tenacity and flexibility. The polyolefin elastomer POE also has excellent thermal-welding property.

Figure 17:
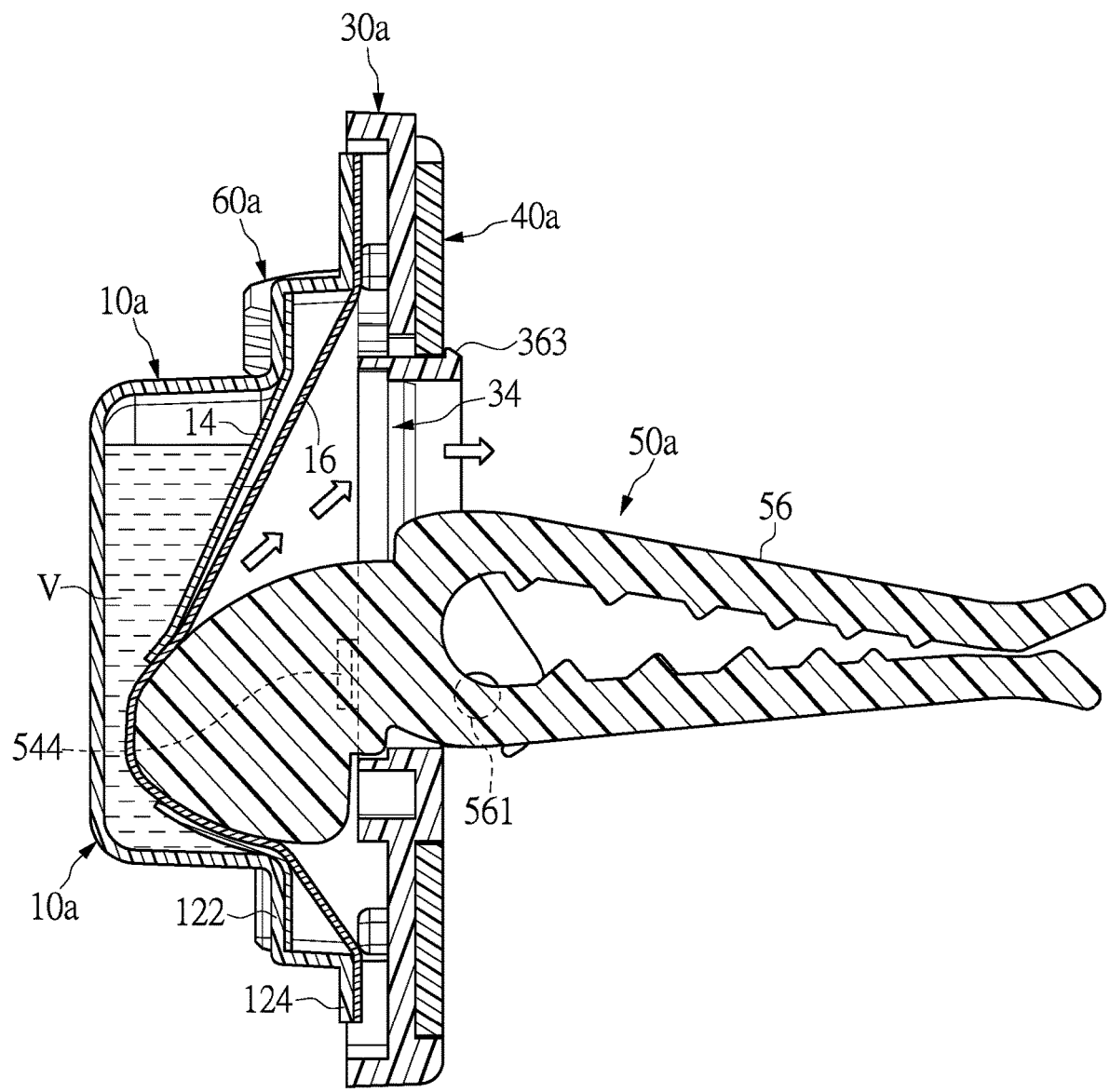
FIG. 17 is a cross-sectional view of the containing apparatus for volatile liquid of the second embodiment in a use state of the present disclosure.

Referring to FIG. 17, which is a cross-sectional view of the containing apparatus for volatile liquid in operation of the second embodiment of the present disclosure. The pressing member 50a rotates for about 90 degrees, and the clipping portion 56 is substantially perpendicular to the rear shell 30a. The penetration plate 54 continuously presses the breathable membrane 16 and then presses rupturable substrate 14. The pressing member 50a of this embodiment further has two engaging portions 544 formed on two sides of the penetration plate 54, respectively. Meanwhile, the engaging portions 544 of the pressing member 50a are engaged with the rear shell 30a, so that the pressing member 50a can be fixed to the rear shell 30a in a position perpendicular to the rear shell 30a. Therefore, the volatile liquid V can flow to the breathable membrane 16 through the breaking hole 140 of the rupturable substrate 14, then the volatile liquid is absorbed by the breathable membrane 16 and slowly vaporizes into the atmosphere.

Third Embodiment

Reference is made to FIG. 18 to FIG. 21, which illustrate a third embodiment according to the present disclosure. The third embodiment provides the containing apparatus for volatile liquid, which includes a container 10b, a rear shell 30b, a pressing member 50b, and an external casing 60b. The pressing member 50b in a non-use state is separated from other elements. When the user wants the volatile liquid to vaporize, the pressing member 50b is inserted to the rear shell 30b, and the volatile liquid in the container 10b can vaporize outwardly. Details of which are described as follows.

Figure 21:
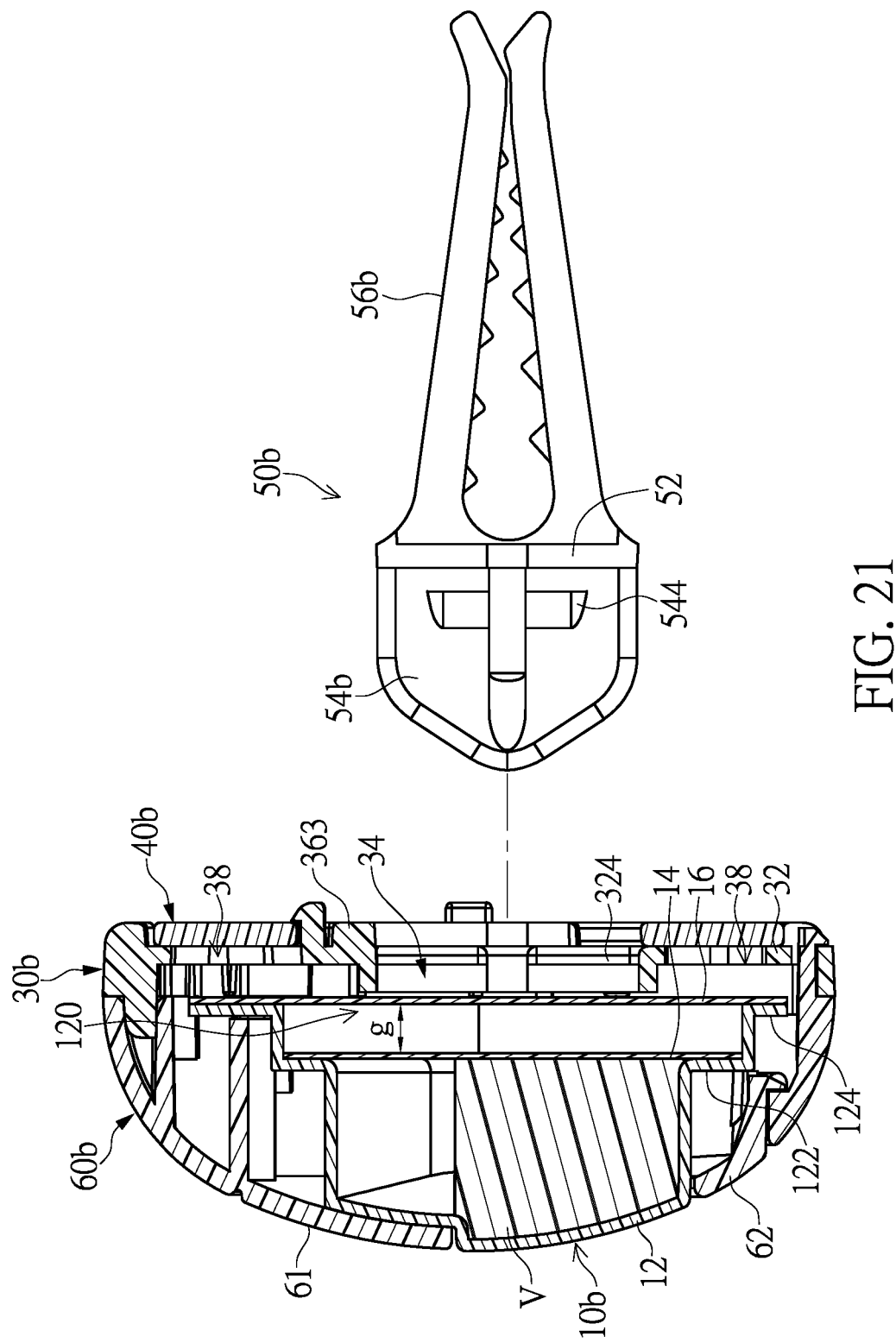
FIG. 21 is a cross-sectional view of the pressing member before being inserted to the rear shell of the third embodiment of the present disclosure.

The container 10b is used to receive and retain the volatile liquid V therein, which includes the accommodating portion 12, the rupturable substrate 14, and the breathable membrane 16. A top end of the accommodating portion 12 has a receiving opening 120. The accommodating portion 12 can be made of plastic. As shown in FIG. 21, an inner rim 122 extends from a top edge of the accommodating portion 12, and the rupturable substrate 14 is adhered to the inner rim 122. In this embodiment, the accommodating portion 12 further has an outer rim 124 outwardly extending from the inner rim 122. A height deviation is formed between the inner rim 122 and the outer rim 124. A shown in the cross-sectional view in FIG. 21, the outer rim 124 is formed at an outer periphery of the inner rim 122. The rupturable substrate 14 is adhered (e.g., by a hot pressing method) to the top surface of the inner rim 122.

The rear shell 30b and the external casing 60b could be combined as a casing, to receive the container 10b. The outer rim 124 of the container 10b abuts against an inner edge of the external casing 60b.

In this embodiment, the rupturable substrate 14 covers the receiving opening 120 of the container 10b. The breathable membrane 16 is disposed at an outer side of the rupturable substrate 14. The "outer side" means a place that is opposite to an inner part of the container 10b. The breathable membrane 16 of this embodiment is adhered to the outer rim 124 of the accommodating portion 12. Details of the rupturable substrate 14 and the breathable membrane 16 have been introduced in the above embodiments, and therefore are not described again.

Figure 22:
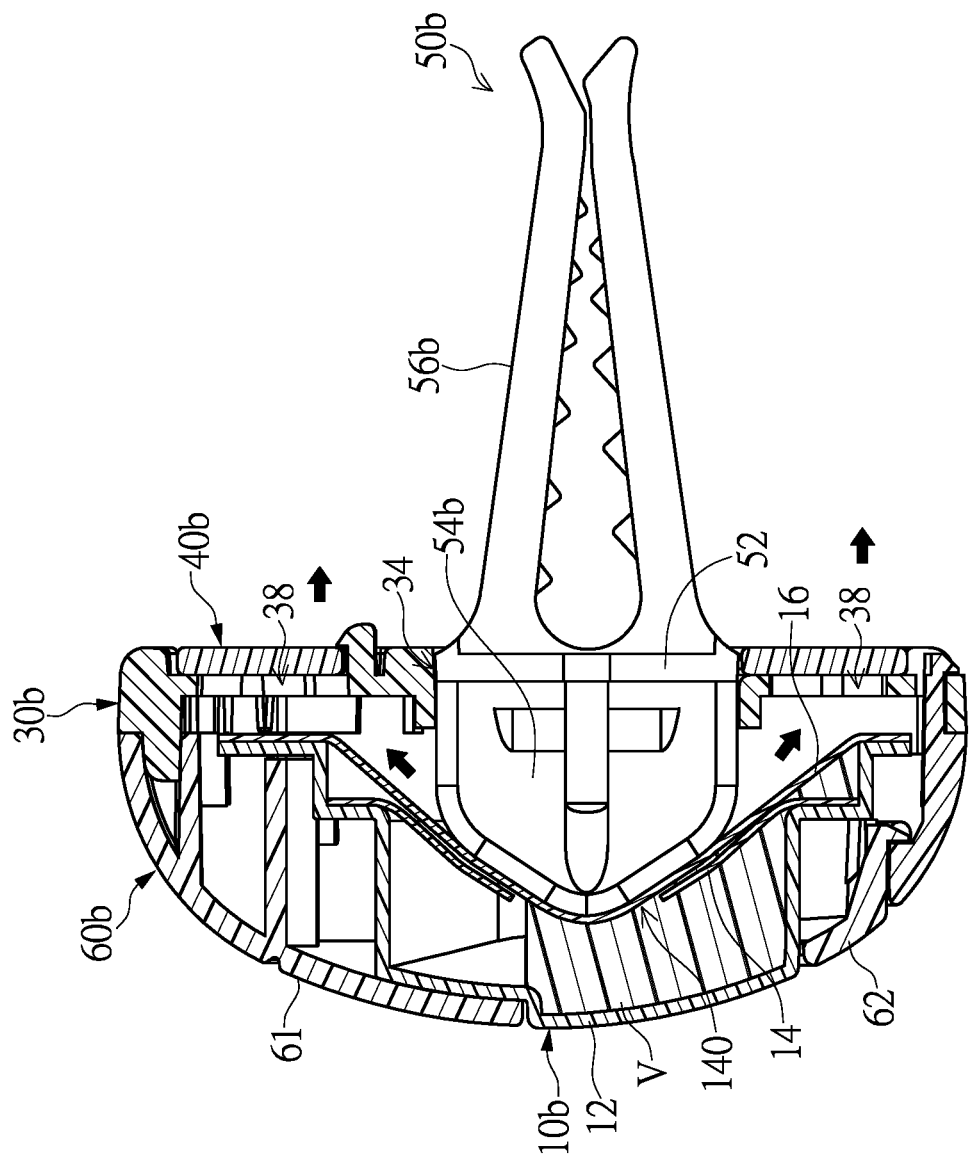
FIG. 22 is an assembled cross-sectional view of the containing apparatus for volatile liquid of the third embodiment of the present disclosure.

The rear shell 30b is disposed at an outer side of the breathable membrane 16, and includes a bottom board 32 and a through-hole 34 forming on the bottom board 32. In this embodiment, the through-hole 34 of the rear shell 30b is cross-shaped. The pressing member 50b in an initial (or non-use) state is separated apart from the rear shell 30b. The breathable membrane 16 is located between the pressing member 50b and the rupturable substrate 14. When the containing apparatus for volatile liquid is used, a front end of the pressing member 50b passes through the through-hole 34 of the rear shell 30b and then breaks the rupturable substrate 14 to form a breaking hole 140 (as shown in FIG. 22). The breathable membrane 16 is with resilience and is not broken by the pressing member 50b, and then, the volatile liquid V passes through the breaking hole 140 of the rupturable substrate 14 and is absorbed by the breathable membrane 16 for vaporizing outside. Therefore, the containing apparatus for volatile liquid of the present disclosure can be retained in a sealed condition during the transporting or storage process, so as to prevent losing the volatile liquid V inside by vaporizing When the user wants to use the volatile liquid V, the user can use the breaking device of the containing apparatus for volatile liquid, that is the pressing member 50b in this embodiment, to break a sealing member of the containing apparatus, so that the volatile liquid V in the containing apparatus can vaporize into the atmosphere. In this embodiment of this present disclosure, a distance between the rupturable substrate 14 and the breathable membrane 16 is changeable according to product design In this embodiment, the pressing member 50b can be an integrated plastic member manufactured by injection molding and functioning as a breaking device, but a material of the pressing member 50b is not limited thereto. For example, it can be made of metal or other materials that are durable enough to exert the pressing force. The pressing member 50b includes a clipping portion 56b and a crushing portion 54b. The crushing portion 54b connects to one end of the clipping portion 56b. The clipping portion 56b can firmly clip to another piece. For example, it can be clipped onto an air vent blade of a mobile device (not shown).

Referring to FIG. 22, after the pressing member 50b is inserted to the container 10b, one end (i.e., the crushing portion 54b) is fixed to the rear shell 30b, and another end (i.e., the clipping portion 56b) can provide a clipping function. When the pressing member 50b is inserted to the rear shell 30b, the crushing portion 54b passes through the through-hole 34 of the rear shell 30b to break the rupturable substrate 14. The shape of the crushing portion 54b of the pressing member 50b corresponds to the shape of the through-hole 34. The crushing portion 54b passes through the through-hole 34 of the rear shell 30b and inwardly presses the breathable membrane 16 and the rupturable substrate 14, yet the breathable membrane 16 is with resilience and is not broken by the pressing member 50b. The crushing portion 54b breaks the rupturable substrate 14. In this embodiment, a front end of the crushing portion 54b of the pressing member 50b is obtuse-shaped, and the clipping portion 56b abuts against the rear shell 30b, so as to limit a length of the crushing portion 54b protruding beyond the through-hole 34. A length of the crushing portion 54b protruding beyond the through-hole 34 is larger than the distance g. However, the pressing member 50b of the present disclosure is not limited to the above structures. For example, the pressing member can be pivotally connected to the rear shell 30b. When the pressing member 50b is in use, the pressing member is rotated to a position perpendicular to the rear shell 30b, and then passes through the through-hole 34 to break the rupturable substrate 14.

Figure 19:
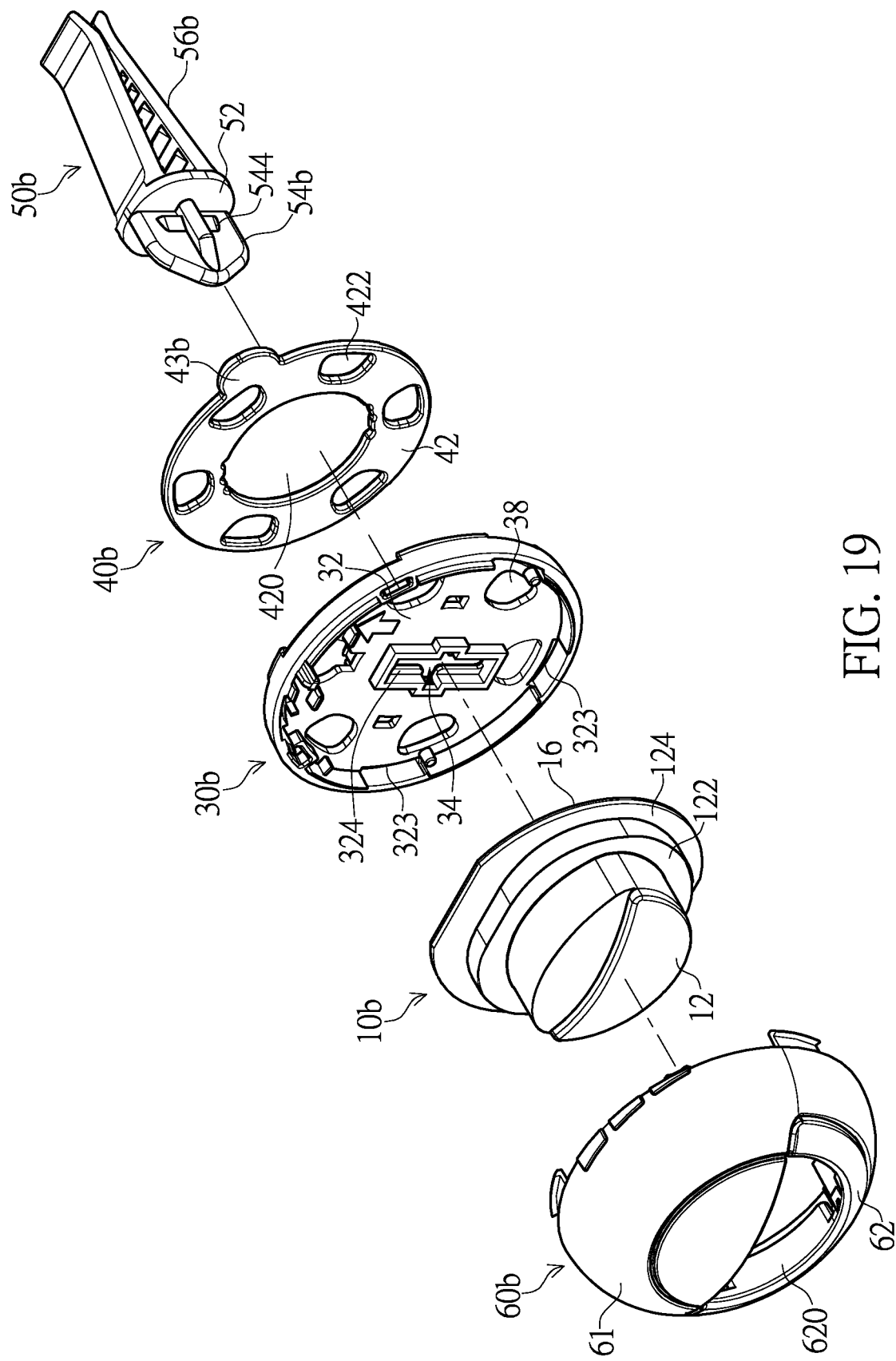
FIG. 19 is another exploded perspective view of the containing apparatus for volatile liquid of the third embodiment of the present disclosure.
Figure 20:
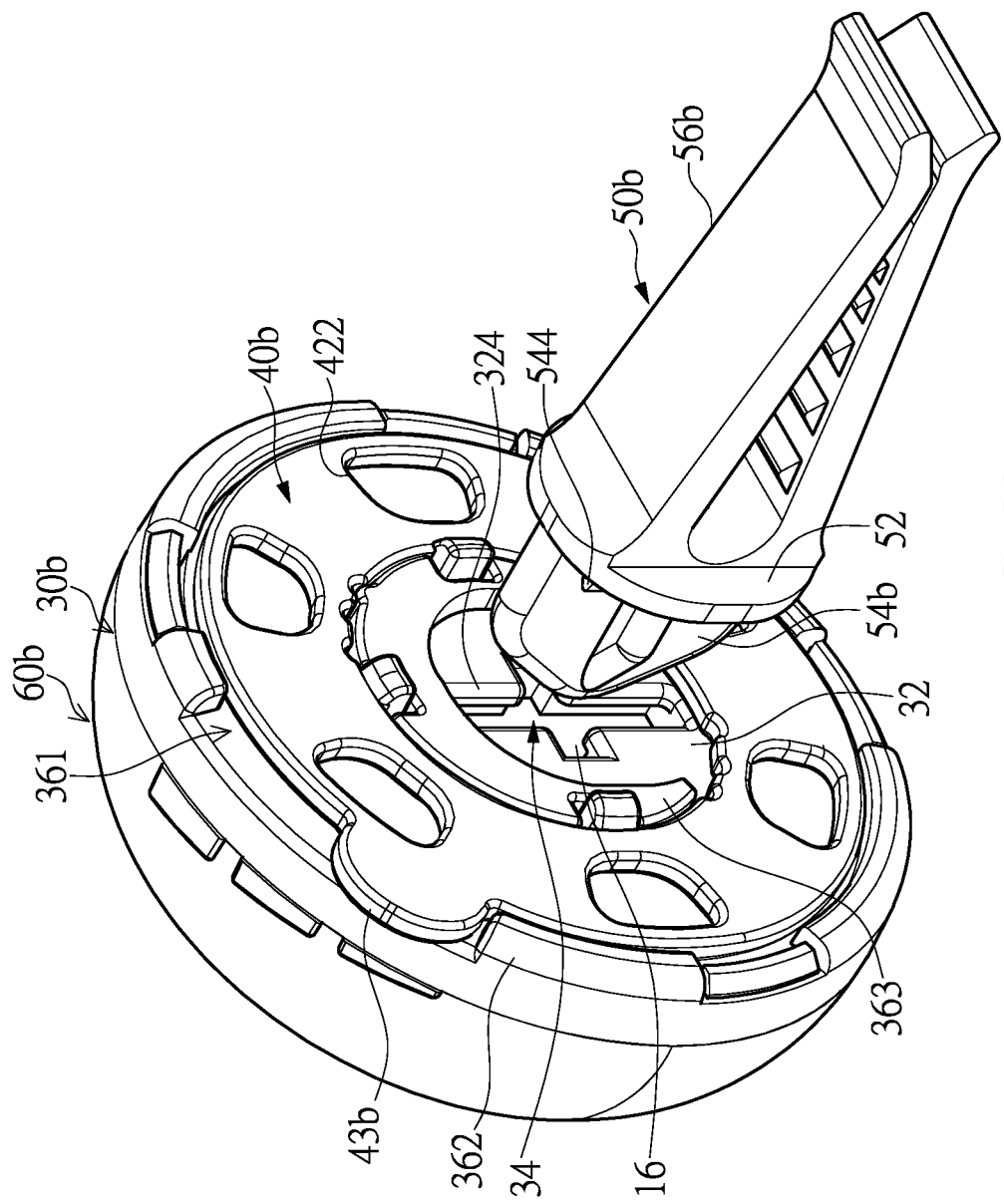
FIG. 20 is a perspective of the pressing member being inserted to the rear shell of the third embodiment of the present disclosure.

In this embodiment, the rear shell 30b is located at an outmost side of the containing apparatus for volatile liquid. As shown in FIGS. 19 and 20, to fix the pressing member 50b to the rear shell 30b, the rear shell 30b includes an engaging portion 324 that inwardly protrudes from the rear shell 30b toward the through-hole 34, and the pressing member 50b has at least one engaging portion 544 formed at one side thereof. According to this embodiment, two sides of the pressing member 50b each have one engaging portion 544. The clipping portion 56b abuts against the rear shell 30b. When the pressing member 50b is arranged at a crushing position, which is the use state, the engaging portions 544 of the pressing member 50b are engaged with the engaging portion 324 of the rear shell 30b, so that the pressing member 50b is fixed to the rear shell 30b.

The rear shell 30b of this embodiment further includes a plurality of vent holes 38, which allows the volatile liquid V to vaporize outwardly through the vent holes 38. In a preferable manner, the containing apparatus for volatile liquid can adjust the vaporizing speed. The containing apparatus for volatile liquid further includes an adjusting element 40b, and a plurality of adjusting openings 422 which are formed on the adjusting element 40b. The rear shell 30b has a plurality of vent holes 38. The adjusting element 40b is rotatably connected to one side of the rear shell 30b, so that the adjusting openings 422 and the vent holes 38 cooperatively form an adjustable ventilation area.

Figure 18:
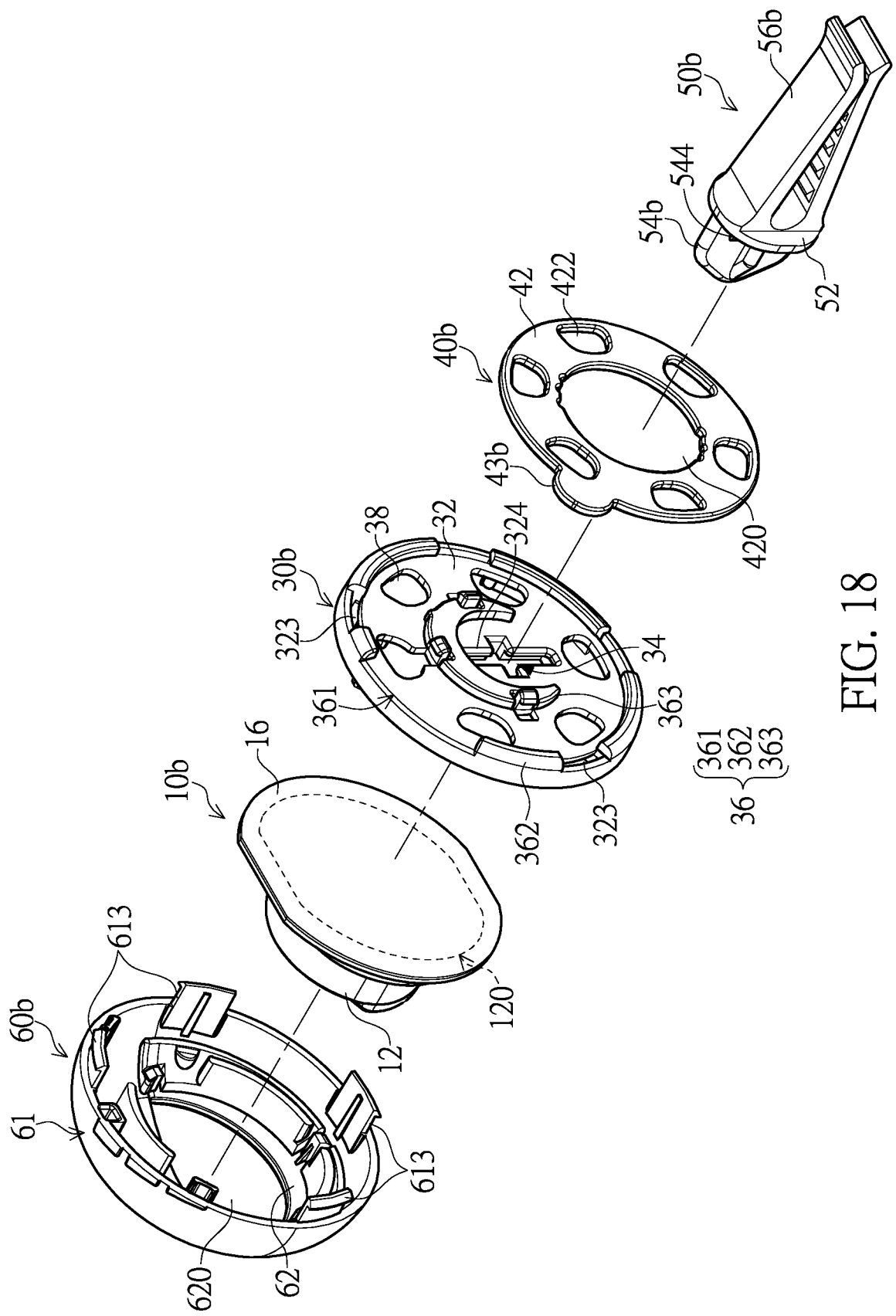
FIG. 18 is an exploded perspective view of the containing apparatus for volatile liquid of a third embodiment of the present disclosure.

Referring to FIG. 18, the adjusting element 40b has an annular-shaped ring portion 42 to define a mounting opening 420. The adjusting element 40b has a grip portion 43b which is formed on an outer edge of the adjusting element 40b. When the grip portion 43b is rotated by the user, the adjusting element 40b can change the position of the adjusting opening 422. A mounting portion 36 is formed on the rear shell 30b. The adjusting element 40b is rotatably connected to the mounting portion 36.

More specifically, in this embodiment, the mounting portion 36 includes an inner annular portion 363 and an outer annular portion 362. The inner annular portion 363 is formed on an external area of the through-hole 34. The outer annular portion 362 is formed on a periphery of the rear shell 30b. The inner annular portion 363 is engaged with an inner edge of the mounting opening 420 of the adjusting element 40b. A position-limiting cutout 361 is formed on the outer annular portion 362. The grip portion 43b is located in the position-limiting cutout 361, so as to limit a displacement range of the grip portion 43b.

Referring to FIG. 18 and FIG. 19, the rear shell 30b and the external casing 60b could be combined as a casing for receiving the container 10b. A combination manner of the external casing 60b and the rear shell 30b could be engagement or adhesion. In this embodiment, the external casing 60b has a plurality of hooks 613, and the rear shell 30b forms a plurality of hooking holes 323 between the outer annular portions 362, so that the external casing 60b can be engaged with the rear shell 30b. In addition, the external casing 60b can be one-piece or multi-pieces. The external casing 60b of this embodiment has an upper casing 61 and a lower casing 62, and both can be in different colors to increase a variety of appearance. The lower casing 62 has an observation window 620, and a part of the accommodating portion 12 of the container 10b is exposed from the observation window 620.

Figure 23:
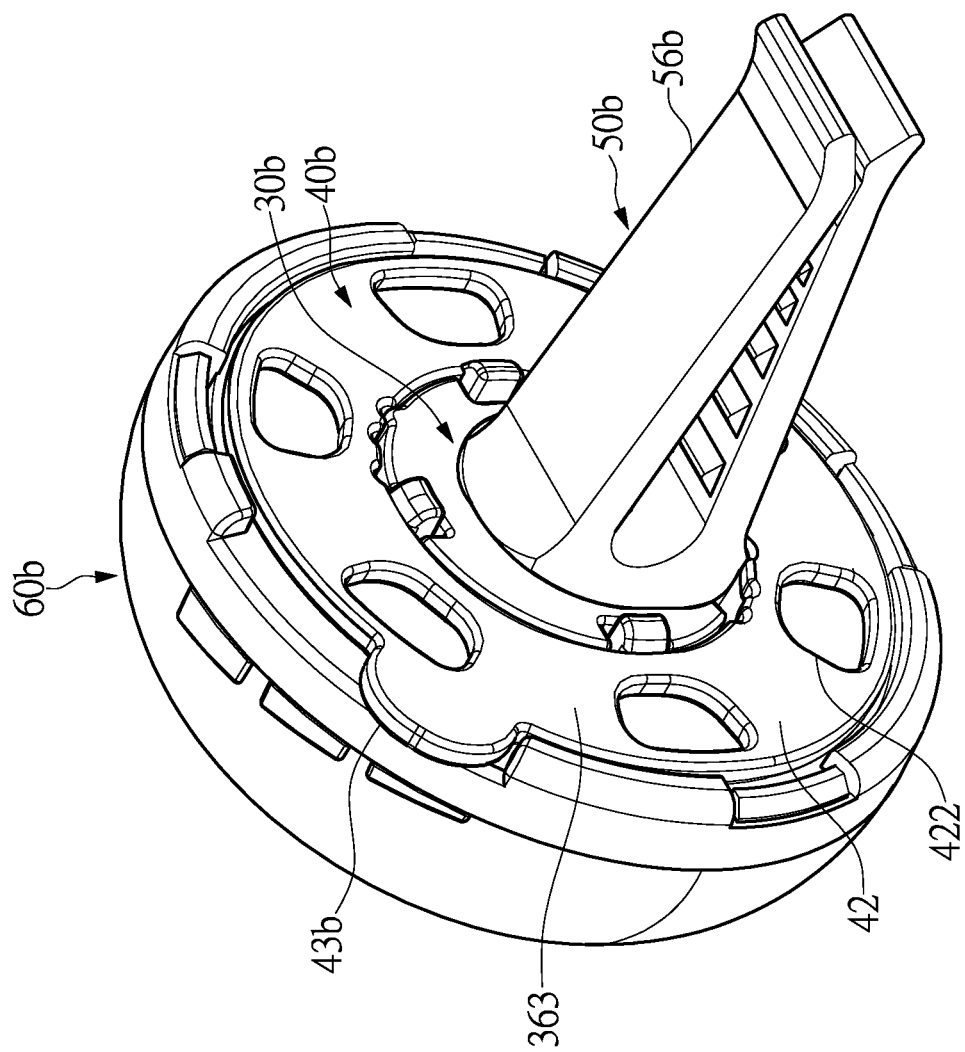
FIG. 23 is an assembled perspective view of the containing apparatus for volatile liquid of the third embodiment of the present disclosure.

As shown in FIG. 22 and FIG. 23, after the pressing member 50b of the containing apparatus for volatile liquid of the present disclosure is inserted to the rear shell 30b, the pressing member 50b is fixed to the back of the rear shell 30b. At the same time, the rupturable substrate 14 forms a breaking hole 140. The volatile liquid flows through the breaking hole 140 of the rupturable substrate 14 by gravity toward the breathable membrane 16. The volatile liquid is absorbed by the breathable membrane 16 and slowly vaporizes into the atmosphere. It should be noted that, the position of the pressing member 50b is preferably close to the bottom of the container 10b, so that the volatile liquid can flow out and vaporize.

Beneficial Effects of the Present Disclosure

The beneficial features of the present disclosure are that, the containing apparatus for volatile liquid provides the pressing member (50, 50a, or 50b) which is movably connected to the rear shell (30, 30a, or 30b), and the breathable membrane 16 is disposed between the pressing member (50, 50a, or 50b) and the rupturable substrate 14. A part of the pressing member (50, 50a, or 50b) passes through the through-hole 34 of the rear shell (30, 30a, or 30b), and breaks the breathable membrane 14 to form a breaking hole. The breathable membrane 16 is with resilience and is not broken by the pressing member (50, 50a, or 50b), so that the volatile liquid passes through the breaking hole of the rupturable substrate 14 and is absorbed by the breathable membrane 16 to vaporize outwardly. Therefore, when the containing apparatus for volatile liquid of the present disclosure is being transported or stored, the volatile liquid is retained under the rupturable substrate 14. If the user wants to use the containing apparatus, the pressing member (50, 50a, or 50b) is pressed or rotated, so as to break the rupturable substrate 14, and the containing apparatus for volatile liquid is not remained in a sealed condition. Therefore, the containing apparatus for volatile liquid according to the present disclosure can be easily stored as well as easily to be used.

Another beneficial feature of the present disclosure is that, regardless of whether the pressing member (50, 50a, or 50b) of the containing apparatus for volatile liquid is being used or not, it can be separated apart from the casing of the containing apparatus for volatile liquid or can be stored in a storage position. Such an arrangement not only can prevent the sealing film from losing the sealing function, but also lower the height of the containing apparatus for volatile liquid for being transported or stored more easily.

The foregoing description of the exemplary embodiments of the disclosure has been presented only for the purposes of illustration and description and is not intended to be exhaustive or to limit the disclosure to the precise forms disclosed. Many modifications and variations are possible in light of the above description.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A containing apparatus for volatile liquid, comprising:
   a container including an accommodating portion for receiving a volatile liquid, the accommodating portion having a receiving opening;
   a rupturable substrate covering the receiving opening of the accommodating portion;
   a breathable membrane, wherein the rupturable substrate is disposed at one side of the breathable membrane, wherein a distance is formed between the breathable membrane and the rupturable substrate at a non-use state;
   a rear shell being disposed at another side of the breathable membrane and having a through-hole; and
   a pressing member movably connected to the rear shell, wherein the breathable membrane is disposed between the pressing member and the rupturable substrate, a part of the pressing member passes through the through-hole of the rear shell and is configured to press on the breathable membrane toward the rupturable substrate from the non-use state to a use state, so that the breathable membrane directly contacts the rupturable substrate, a part of the rupturable substrate is compressed forcefully by the breathable membrane and the rupturable substrate is crushed to form a breaking hole at the use state, and the breathable membrane is stretchable and not broken by the pressing member, so that the volatile liquid passes through the breaking hole of the rupturable substrate and is absorbed by the breathable membrane for vaporizing into the atmosphere;
   wherein the pressing member includes a clipping portion and a crushing portion, the crushing portion is connected to one end of the clipping portion, and the crushing portion penetrates the through-hole of the rear shell to break the rupturable substrate at the use state, so as to limit a length of the crushing portion protruding beyond the through-hole;
   wherein the length of the crushing portion protruding beyond the through-hole at the use state is larger than the distance between the breathable membrane and the rupturable substrate at the non-use state, and over an original position of the breathable membrane in the non-use state, so that the crushing portion is capable to crush the rupturable substrate but remain the breathable membrane in an unbroken state.

2. The containing apparatus for volatile liquid according to claim 1, wherein the pressing member includes a top board and a penetration plate, the penetration plate is connected with a bottom surface of the top board, one side of the top board is pivotally connected with the rear shell, and the penetration plate passes through the through-hole of the rear shell to break the rupturable substrate; wherein the rear shell has a basin portion, the basin portion is concavely formed on a top surface of the rear shell, and the through-hole is formed on the basin portion to form a limiting mechanism to limit a position of the pressing member; wherein when the pressing member is located at a pressed-down position, the top board of the pressing member is received in the basin portion, and the penetration plate is exposed from a bottom of the rear shell.

3. The containing apparatus for volatile liquid according to claim 2, wherein the rear shell includes a rotary shaft, the rotary shaft is located at one end of the through-hole, the pressing member has a pivoting portion, and the pivoting portion is connected rotatably with the rotary shaft, wherein the pivoting portion of the pressing member is perpendicular to the penetration plate.

4. The containing apparatus for volatile liquid according to claim 1, wherein the accommodating portion has an inner rim extending outward from a top edge thereof, the rupturable substrate is adhered to a top surface of the inner rim, the inner rim has a top edge extending outward, and the breathable membrane is adhered to the top edge of the inner rim.

5. The containing apparatus for volatile liquid according to claim 1, further comprising an adjusting element, wherein a plurality of adjusting openings are formed on the adjusting element, the rear shell includes a plurality of vents, and the adjusting element is rotatably disposed at one side of the rear shell so that the adjusting openings and the vents cooperatively form an adjustable ventilation area.

6. The containing apparatus for volatile liquid according to claim 5, wherein the adjusting element is annular-shaped and a mounting opening is formed therein, the adjusting element has a grip portion formed on an outer edge of the adjusting element, the rear shell has a mounting portion, and the adjusting element is rotatably connected to the mounting portion.

7. The containing apparatus for volatile liquid according to claim 6, wherein the mounting portion includes an inner annular portion and an outer annular portion, the inner annular portion is formed on a periphery of the through-hole, the outer annular portion is formed on a peripheral edge of the rear shell, the inner annular portion engages with an inner edge of the mounting opening of the adjusting element, the outer annular portion has a position-limiting cutout, and the grip portion is located in the position-limiting cutout so as to limit a displacement range of the grip portion.

8. The containing apparatus for volatile liquid according to claim 1, wherein the pressing member includes a clipping portion and a penetration plate, the penetration plate is connected to one end of the clipping portion, and the clipping portion is pivotally connected to the rear shell, so that the pressing member is rotatable around an axis, wherein by rotating the pressing member from a storage state to an use state, the penetration plate is configured to penetrate the through-hole of the rear shell and inwardly press on the breathable membrane and the rupturable substrate, wherein a distance from one side of the penetration plate close to the container to the axis is smaller than a distance from a top end of the penetration plate to the axis.

9. The containing apparatus for volatile liquid according to claim 8, wherein an engaging portion is formed at two sides of the penetration plate of the pressing member respectively, and when the pressing member rotates to the use state, the engaging portion is engaged with the rear shell, so that the pressing member is fixed to the rear shell.

10. The containing apparatus for volatile liquid according to claim 1, wherein an engaging portion is formed on the rear shell, the engaging portion protrudes from the rear shell toward the through-hole, at least one engaging portion is formed on one side of the pressing member, and the clipping portion abuts against the rear shell; when the pressing member moves to a crushing position, the at least one engaging portion of the pressing member is engaged with the engaging portion of the rear shell, so that the pressing member is fixed to the rear shell.

11. The containing apparatus for volatile liquid according to claim 10, wherein a front end of the crushing portion of the pressing member is obtuse-shaped, and the clipping portion abuts against the rear shell so as to limit a length of the crushing portion protruding beyond the through-hole.

12. The containing apparatus for volatile liquid according to claim 1, further comprising an external casing, wherein the rear shell and the external casing are combined as a casing to receive the container, an observation window is formed on the external casing, and a part of the accommodating portion of the container is exposed from the observation window.

13. The containing apparatus for volatile liquid according to claim 1, wherein the distance between the breathable membrane and the rupturable substrate is from 0.2 mm to 7 mm.

14. The containing apparatus for volatile liquid according to claim 1, wherein a stretching rate of the breathable membrane is from 200% to 990%.

* * * * *